(12) United States Patent
Ravenscroft et al.

(10) Patent No.: US 10,004,842 B2
(45) Date of Patent: *Jun. 26, 2018

(54) METHOD AND APPARATUS FOR THE DIALYSIS OF BLOOD

(71) Applicant: Medical Components, Inc., Harleysville, PA (US)

(72) Inventors: Adrian Ravenscroft, Cohasset, MA (US); Donald Woods, Duxbury, MA (US)

(73) Assignee: Medical Components, Inc., Harleysville, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/728,026

(22) Filed: Jun. 2, 2015

(65) Prior Publication Data

US 2016/0114093 A1 Apr. 28, 2016

Related U.S. Application Data

(63) Continuation of application No. 13/584,177, filed on Aug. 13, 2012, now Pat. No. 9,044,573.

(Continued)

(51) Int. Cl.
*A61M 25/01* (2006.01)
*A61M 25/14* (2006.01)
(Continued)

(52) U.S. Cl.
CPC ........ *A61M 1/3661* (2014.02); *A61M 1/3659* (2014.02); *A61M 25/003* (2013.01);
(Continued)

(58) Field of Classification Search
CPC .............. A61M 1/3659; A61M 1/3661; A61M 2025/0031; A61M 2025/0037;
(Continued)

(56) References Cited

U.S. PATENT DOCUMENTS 2,972,779 A   2/1961  Cowley
3,965,901 A * 6/1976  Penny ................ A61M 25/007
                                                  604/119

(Continued)

*Primary Examiner* — Adam Marcetich
(74) *Attorney, Agent, or Firm* — Buchanan Ingersoll & Rooney PC

(57) ABSTRACT

Apparatus for use in dialyzing a patient comprising a hemodialysis catheter comprising an elongated body having a proximal and a distal end, wherein the distal end terminates in a substantially planar distal end surface; first and second lumens extending from the proximal end to the distal end, wherein the lumens terminate on the distal end surface in first and second mouths, arranged in side-by-side configuration, and further wherein the lumens are separated by a septum; and first and second longitudinal slots formed in the distal end of the elongated body and communicating with the interiors of the lumens, the slots opening on the distal end surface; wherein the slots each have a length and a width, relative to the dimensions of the lumens and the rate of blood flow to be passed through the hemodialysis catheter, so as to minimize undesirable recirculation of dialyzed blood. given lumen is to be used for a suction function, the primary blood flow will enter the proximal end of the longitudinal slot associated with that lumen, whereby to minimize undesirable recirculation of dialyzed blood.

17 Claims, 38 Drawing Sheets

Related U.S. Application Data

(60) Provisional application No. 61/522,568, filed on Aug. 11, 2011, provisional application No. 61/638,079, filed on Apr. 25, 2012.

(51) Int. Cl.
  *A61M 25/00* (2006.01)
  *A61M 1/36* (2006.01)
  *A61M 39/22* (2006.01)
  *A61M 39/08* (2006.01)

(52) U.S. Cl.
  CPC ...... *A61M 25/007* (2013.01); *A61M 25/0021* (2013.01); *A61M 25/0026* (2013.01); *A61M 25/0067* (2013.01); *A61M 25/0071* (2013.01); *A61M 25/0194* (2013.01); *A61M 39/22* (2013.01); *A61M 2025/0031* (2013.01); *A61M 2025/0037* (2013.01); *A61M 2025/0073* (2013.01); *A61M 2039/082* (2013.01); *A61M 2039/226* (2013.01)

(58) Field of Classification Search
  CPC .... A61M 2025/0073; A61M 2039/082; A61M 2039/226; A61M 25/0021; A61M 25/0026; A61M 25/003; A61M 25/0067; A61M 25/007; A61M 25/0071; A61M 25/0194; A61M 39/22
  See application file for complete search history.

(56) References Cited

U.S. PATENT DOCUMENTS

| | | | |
|---|---|---|---|
| 4,639,246 A | 1/1987 | Dudley | |
| 4,895,561 A | 1/1990 | Mahurkar | |
| 5,009,636 A | 4/1991 | Wortley et al. | |
| 5,112,301 A | 5/1992 | Fenton, Jr. et al. | |
| 5,190,520 A * | 3/1993 | Fenton, Jr. | A61M 25/005 604/43 |
| 5,195,962 A | 3/1993 | Martin et al. | |
| 5,209,723 A | 5/1993 | Twardowski et al. | |
| 5,395,316 A | 3/1995 | Martin | |
| 5,405,320 A | 4/1995 | Twardowski et al. | |
| 5,472,417 A | 12/1995 | Martin et al. | |
| 5,536,261 A | 7/1996 | Stevens | |
| 5,569,182 A | 10/1996 | Twardowski et al. | |
| 5,685,867 A | 11/1997 | Twardowski et al. | |
| 5,693,030 A | 12/1997 | Lee et al. | |
| 5,797,869 A | 8/1998 | Martin et al. | |
| 5,830,196 A | 11/1998 | Hicks | |
| 5,961,486 A | 10/1999 | Twardowski et al. | |
| 5,976,114 A | 11/1999 | Jonkman et al. | |
| 6,096,798 A | 8/2000 | Luthra et al. | |
| 6,102,884 A | 8/2000 | Squitieri | |
| 6,206,849 B1 | 3/2001 | Martin et al. | |
| 6,406,687 B1 | 6/2002 | Luthra et al. | |
| 6,409,700 B1 | 6/2002 | Siegel, Jr. et al. | |
| 6,461,321 B1 | 10/2002 | Quinn | |
| 6,540,714 B1 | 4/2003 | Quinn | |
| 6,582,409 B1 | 6/2003 | Squitieri | |
| 6,702,776 B2 | 3/2004 | Quinn | |
| 6,758,836 B2 | 7/2004 | Zawacki | |
| 6,969,373 B2 | 11/2005 | Schwartz et al. | |
| 7,034,061 B1 | 4/2006 | Luthra et al. | |
| 7,090,654 B2 | 8/2006 | Lotito et al. | |
| 7,141,035 B2 | 11/2006 | Haggstrom | |
| 7,182,746 B2 | 2/2007 | Haarala et al. | |
| D540,467 S | 4/2007 | Mori | |
| D541,936 S | 5/2007 | Patterson | |
| 7,211,074 B2 | 5/2007 | Sansoucy | |
| 7,229,429 B2 | 6/2007 | Martin et al. | |
| D550,839 S | 9/2007 | Zawacki et al. | |
| 7,322,953 B2 | 1/2008 | Redinger | |
| 7,393,339 B2 | 1/2008 | Redinger | |
| D581,529 S | 11/2008 | Moehle et al. | |
| 7,569,029 B2 | 8/2009 | Clark | |
| D603,044 S | 10/2009 | Appling et al. | |
| 7,655,000 B2 | 2/2010 | Walls et al. | |
| RE41,448 E | 7/2010 | Squitieri | |
| 7,776,005 B2 | 8/2010 | Haggstrom et al. | |
| D640,788 S | 6/2011 | Appling | |
| 8,021,321 B2 | 9/2011 | Zawacki | |
| 8,066,660 B2 | 11/2011 | Gregersen et al. | |
| 8,092,415 B2 | 1/2012 | Moehle et al. | |
| 8,123,892 B2 | 2/2012 | Morris et al. | |
| D657,461 S | 4/2012 | Schembre et al. | |
| 8,152,951 B2 | 4/2012 | Zawacki et al. | |
| 8,292,841 B2 | 10/2012 | Gregersen | |
| 8,323,227 B2 | 12/2012 | Hamatake et al. | |
| 8,337,451 B2 | 12/2012 | Lareau et al. | |
| 8,403,911 B2 | 3/2013 | Adams et al. | |
| 8,454,565 B2 | 6/2013 | Braga et al. | |
| 8,496,607 B2 | 7/2013 | Feng et al. | |
| 8,496,629 B2 | 7/2013 | McKinnon et al. | |
| 8,500,939 B2 | 8/2013 | Nimkar et al. | |
| 8,517,978 B2 | 8/2013 | Clark | |
| D690,009 S | 9/2013 | Schembre et al. | |
| 8,540,661 B2 | 9/2013 | Gregersen | |
| RE44,639 E | 12/2013 | Squitieri | |
| 8,636,682 B2 | 1/2014 | Deshpande | |
| 8,679,091 B2 | 3/2014 | Morris et al. | |
| 8,696,614 B2 | 4/2014 | Gregersen et al. | |
| 8,747,343 B2 | 6/2014 | MacMeans et al. | |
| 8,808,227 B2 | 8/2014 | Zawacki et al. | |
| 8,894,601 B2 | 11/2014 | Moehle et al. | |
| 8,894,607 B2 | 11/2014 | Barrett et al. | |
| 8,920,404 B2 | 12/2014 | Ditiore et al. | |
| 9,005,154 B2 | 4/2015 | Matson et al. | |
| 9,056,183 B2 | 6/2015 | Deshpande | |
| D736,916 S | 8/2015 | Appling et al. | |
| 9,138,567 B2 | 9/2015 | Pruitt et al. | |
| 9,155,862 B2 | 10/2015 | Bellisario et al. | |
| 9,168,355 B2 | 10/2015 | Braga | |
| 9,174,019 B2 | 11/2015 | Gregersen | |
| 9,192,710 B2 | 11/2015 | Feng et al. | |
| D748,252 S | 1/2016 | King et al. | |
| 9,233,200 B2 | 1/2016 | Gregersen et al. | |
| 9,238,122 B2 | 1/2016 | Malhi et al. | |
| 9,248,253 B2 | 2/2016 | Melsheimer et al. | |
| 9,333,321 B2 | 5/2016 | Clark | |
| 9,387,304 B2 | 7/2016 | Zawacki et al. | |
| 9,399,112 B2 | 7/2016 | Shevgoor et al. | |
| D767,127 S | 9/2016 | de Beer | |
| 9,463,300 B2 | 10/2016 | Pruitt et al. | |
| 9,526,861 B2 | 12/2016 | Bellisario et al. | |
| 9,579,485 B2 | 2/2017 | Oborn et al. | |
| 9,610,422 B2 | 4/2017 | Moehle et al. | |
| 9,642,962 B2 | 5/2017 | Matson et al. | |
| 9,656,041 B2 | 5/2017 | Hamatake et al. | |
| 9,687,269 B2 | 6/2017 | Parent | |
| 9,713,694 B2 | 7/2017 | Braga et al. | |
| 2003/0144623 A1 * | 7/2003 | Heath | A61M 25/0023 604/4.01 |
| 2004/0006318 A1 | 1/2004 | Periakaruppan et al. | |
| 2004/0006331 A1 * | 1/2004 | Shchervinsky | A61M 1/008 604/541 |
| 2004/0193102 A1 | 9/2004 | Haggstrom | |
| 2005/0033264 A1 | 2/2005 | Redinger | |
| 2005/0182352 A1 | 8/2005 | DiMatteo et al. | |
| 2005/0197633 A1 | 9/2005 | Schwartz et al. | |
| 2005/0267400 A1 | 12/2005 | Haarala et al. | |
| 2006/0004316 A1 | 1/2006 | Ditiore et al. | |
| 2006/0100872 A1 | 5/2006 | Yokoi | |
| 2006/0189922 A1 | 8/2006 | Amarasinghe et al. | |
| 2007/0078437 A1 | 4/2007 | Borden et al. | |
| 2007/0123811 A1 | 5/2007 | Squitieri | |
| 2008/0082079 A1 | 4/2008 | Braga et al. | |
| 2009/0005762 A1 * | 1/2009 | Nishtala | A61M 27/00 604/541 |
| 2009/0093748 A1 * | 4/2009 | Patterson | A61M 25/003 604/6.16 |
| 2009/0118661 A1 * | 5/2009 | Moehle | A61M 25/0068 604/6.16 |

(56) References Cited

U.S. PATENT DOCUMENTS

| | | |
|---|---|---|
| 2009/0187141 A1 | 7/2009 | Lareau et al. |
| 2011/0077577 A1 | 3/2011 | Sansoucy |
| 2011/0130745 A1 | 6/2011 | Shevgoor et al. |
| 2011/0137225 A1 | 6/2011 | Feng et al. |
| 2011/0172642 A1 | 7/2011 | Lareau |
| 2013/0053763 A1 | 2/2013 | Makino et al. |
| 2013/0085438 A1 | 4/2013 | MacMeans et al. |
| 2013/0085477 A1 | 4/2013 | Deshpande |
| 2013/0253445 A1 | 9/2013 | Nimkar et al. |
| 2013/0289532 A1 | 10/2013 | McKinnon et al. |
| 2014/0012209 A1 | 1/2014 | Sansoucy |
| 2014/0018772 A1 | 1/2014 | Ash |
| 2014/0316382 A1 | 10/2014 | Morris et al. |
| 2015/0306302 A1 | 10/2015 | Marsden et al. |
| 2016/0051745 A1 | 2/2016 | Gregersen |
| 2016/0121040 A1 | 5/2016 | Gregersen et al. |
| 2016/0128715 A1 | 5/2016 | Malhi et al. |
| 2016/0250441 A1 | 9/2016 | Clark |
| 2016/0325072 A1 | 11/2016 | Shevgoor et al. |
| 2017/0035987 A1 | 2/2017 | Ardehali |
| 2017/0100560 A1 | 4/2017 | Bellisario et al. |
| 2017/0165453 A1 | 6/2017 | Oborn et al. |

\* cited by examiner

VISUALIZATION OF BLOOD FLOW USING
COMPUTATIONAL FLUID DYNAMICS (CFD) MODEL

CATHETER DIAMETER: 15.5 FRENCH
D-SHAPED LUMEN, LONG DIMENSION (195): 3.5 mm
D-SHAPED LUMEN, SHORT DIMENSION (200): 1.5 mm
LONGITUDINAL SLOT LENGTH: 21mm
LONGITUDINAL SLOT WIDTH: 1.5 mm

Catheter flow = 350 ml/min
Tube flow = 1600 ml/min

SUCTION BLOOD FLOW
RETURN BLOOD FLOW

FIG. 14

VISUALIZATION OF BLOOD FLOW USING
COMPUTATIONAL FLUID DYNAMICS (CFD) MODEL

CATHETER DIAMETER: 15.5 FRENCH
D-SHAPED LUMEN, LONG DIMENSION (195): 3.5 mm
D-SHAPED LUMEN, SHORT DIMENSION (200): 1.5 mm
LONGITUDINAL SLOT LENGTH: 21mm
LONGITUDINAL SLOT WIDTH: 1.5 mm

Catheter flow = 450 ml/min
Tube flow = 1600 ml/min

SUCTION BLOOD FLOW
RETURN BLOOD FLOW

FIG. 13

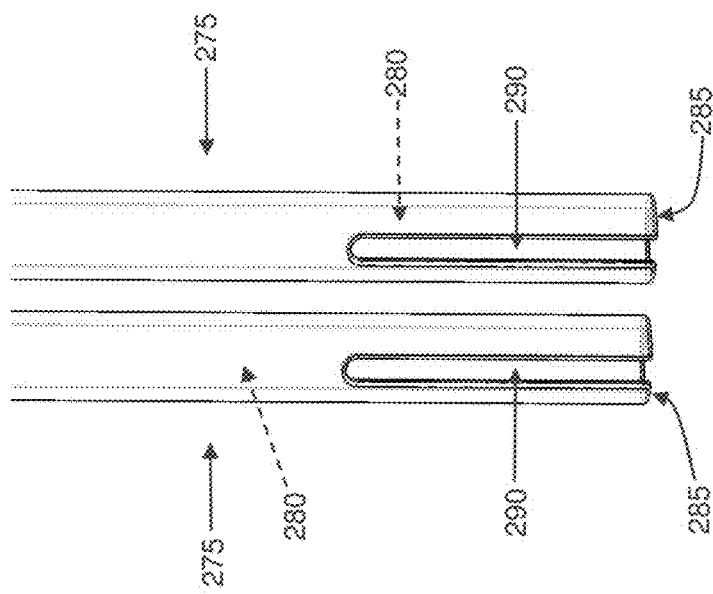

METHOD AND APPARATUS FOR THE DIALYSIS OF BLOOD

REFERENCE TO PENDING PRIOR PATENT APPLICATIONS

This patent application is a continuation of pending prior U.S. patent application Ser. No. 13/584,177, filed Aug. 13, 2012 by Adrian Ravenscroft et al. for METHOD AND APPARATUS FOR THE DIALYSIS OF BLOOD, which in turn claims benefit of:

(i) prior U.S. Provisional Patent Application Ser. No. 61/522,568, filed Aug. 11, 2011 by Adrian Ravenscroft et al. for APPARATUS AND METHOD FOR THE DIALYSIS OF BLOOD; and (ii) prior U.S. Provisional Patent Application Ser. No. 61/638,079, filed Apr. 25, 2012 by Adrian Ravenscroft et al. for METHOD AND APPARATUS FOR THE DIALYSIS OF BLOOD.

The three (3) above-identified patent applications are hereby incorporated herein by reference.

FIELD OF THE INVENTION

This invention relates to the dialysis of blood in general, and more particularly to methods and apparatus for use in the same.

BACKGROUND OF THE INVENTION

A healthy kidney removes toxic wastes and excess water from the blood. In End Stage Renal Disease ("ESRD"), or chronic kidney failure, the kidneys progressively stop performing these essential functions over a long period of time. When the kidneys fail, a patient dies within a short period of time unless that patient receives dialysis treatment for the rest of that patient's life or undergoes transplantation of a healthy, normal kidney. Since relatively few kidneys are currently available for transplantation, the overwhelming majority of patients with ESRD receive dialysis treatment.

Hemodialysis therapy is an extracorporeal (i.e., outside the body) process which removes toxins and water from a patient's blood. A hemodialysis machine pumps blood from the patient, through a dialyzer, and then back into the patient. The dialyzer removes the toxins and water from the blood by a membrane diffusion process. Typically, a patient with chronic kidney disease requires hemodialysis treatments three times per week, for 3-6 hours per session.

Thus, hemodialysis treatments require repetitive access to the vascular system of the patient.

One common method for repetitively accessing the vascular system of a patient for hemodialysis involves the use of a percutaneous catheter. The percutaneous catheter is inserted into a major vein, such as a femoral, subclavian or jugular vein. For long term maintenance dialysis, a jugular vein is generally the preferred insertion site. The catheter is percutaneous, with one end external to the body and the other end dwelling in either the superior vena cava or the right atrium of the heart. The external portion of the catheter has connectors permitting attachment of blood lines leading to and from the hemodialysis machine.

FIGS. 1 and 2 show a typical prior art hemodialysis catheter 5 disposed in the body of a patient. More particularly, hemodialysis catheter 5 generally comprises a catheter portion 10 comprising a dual-lumen catheter element 15, and a connector portion 20 comprising an extracorporeal connector element 25. The catheter's extracorporeal connector element 25 is disposed against the chest 30 of the patient, with the distal end 35 of catheter element 15 extending down the patient's jugular vein 40 and into the patient's superior vena cava 45. More particularly, the distal end 35 of dual-lumen catheter element 15 is positioned within the patient's superior vena cava 45 such that the mouth 50 of the suction line (i.e., lumen) 55, and the mouth 60 of the return line (i.e., lumen) 65, are both located between the patient's right atrium 70 and the patient's left subclavia vein 75 and right subclavia vein 80. Alternatively, the distal end 35 of dual-lumen catheter element 15 may be positioned so that mouth 50 of suction line 55, and mouth 60 of return line 65, are located within the patient's right atrium 70. The hemodialysis catheter 5 is then left in this position relative to the body, waiting to be used during an active dialysis session.

When hemodialysis is to be performed on a patient, the catheter's extracorporeal connector element 25 is appropriately connected to a dialysis machine (not shown), i.e., suction line 55 is connected to the suction port of the dialysis machine, and return line 65 is connected to the return port of the dialysis machine. The dialysis machine is then activated (i.e., the dialysis machine's blood pump is turned on and the flow rate set), whereupon the dialysis machine will withdraw relatively "dirty" blood from the patient through suction line 55 and return relatively "clean" blood to the patient through return line 65.

In order to minimize clotting within the hemodialysis catheter between dialysis sessions, the lumens of the hemodialysis catheter are typically filled with a diluted heparin solution (i.e., a "lock solution") between the dialysis sessions. More particularly, after a dialysis session has been completed, a diluted heparin solution (i.e., the "lock solution") is loaded into the lumens of the hemodialysis catheter and clamps set at the proximal end of the hemodialysis catheter (i.e., at the catheter's extracorporeal connector element 25). These clamps prevent the lock solution from draining out of the distal end of the catheter into systemic circulation. At the start of a hemodialysis session, the clamps are released and the lock solution is withdrawn from the hemodialysis catheter, whereupon the hemodialysis catheter is ready for use in a dialysis procedure.

It will be appreciated that the efficiency of a hemodialysis procedure will be reduced if there is recirculation of the dialyzed blood flow, i.e., if the cleansed blood returning to the body through the return line 65 is immediately drawn back into the suction line 55. To avoid this problem, hemodialysis catheters have traditionally staggered the openings 50, 60 of the lines 55, 65, respectively, in the manner shown in FIG. 2, i.e., so that mouth 60 of return line 65 is disposed distal to mouth 50 of suction line 55. With this arrangement, given the direction of the blood flow in superior vena cava 45, mouth 60 of return line 65 is always disposed "downstream" of mouth 50 of suction line 55. As a result, there is a reduced possibility that the cleansed blood returning to the body through return line 65 will be immediately drawn back into suction line 55, and hence any undesirable recirculation of the cleansed blood flow is minimized.

One consequence of forming the hemodialysis catheter with the aforementioned "staggered tip" configuration (i.e., so that mouth 60 of return line 65 is disposed distal to mouth 50 of suction line 55) is that each lumen of the dual-lumen hemodialysis catheter is effectively dedicated to a particular function, i.e., line 65 is limited to use as a return line and line 55 is limited to use as a suction line. This point becomes clear if one considers the effect of reversing the use of each line, i.e., of using line 65 as a suction line and of using line 55 as a return line—in this reversed situation, the undesirable recirculation of the cleansed blood would tend to increase significantly, since the cleansed blood emerging from the mouth of the return line would be released just upstream of the mouth of the suction line, so that the cleansed blood would tend to be drawn back into the mouth of the suction line immediately after being returned to the body. As a result, there would be a significant reduction in the efficiency of a hemodialysis procedure (e.g., 15-30%, depending on the catheter tip design), and hence dialysis sessions would need to increase significantly in duration and/or frequency. Furthermore, if such a line reversal were to occur inadvertently and escape the attention of the attending medical personnel, the reduced hemodialysis efficiency might cause a patient to unknowingly receive inadequate dialysis during a treatment session, which could have serious health consequences for the patient.

The requirement that each line be dedicated to a particular function (i.e., suction or return, depending on whether its mouth is disposed proximal or distal to the mouth of its counterpart line) can be problematic in certain situations.

By way of example but not limitation, if a blood clot were to form in the suction line, it could be desirable to reverse flow through this line to see if the blood clot could be cleared from the catheter by forcing the blood clot out the distal end of the catheter. However, this approach requires the aforementioned line reversal, with the suction line being used as the return line and the return line being used as the suction line. As noted above, such line reversal is problematic where the hemodialysis catheter utilizes the aforementioned "staggered tip" construction.

By way of further example but not limitation, where the disposition of the hemodialysis catheter within the vascular system of the patient is such that suction from the suction line causes the hemodialysis catheter to repeatedly adhere to a vascular wall, it could be desirable to reverse flow through this line to avoid such recurrent adhesion. However, as noted above, such line reversal is problematic where the hemodialysis catheter utilizes the aforementioned "staggered tip" construction, since the mouth of the suction line should be disposed upstream of the mouth of the return line in order to minimize the recirculation of dialyzed blood.

The requirement that each line be dedicated to a particular function (i.e., suction or return, depending on whether its mouth is disposed proximal or distal to the mouth of its counterpart line) is eliminated if the two lines of the dialysis catheter co-terminate, i.e., if the mouths of the two lines are disposed in a side-by-side configuration, such as that shown in FIG. 3. This construction can be highly desirable, since it eliminates the need to dedicate a particular line to a particular function, and hence would greatly simplify dialysis setup and provide increased flexibility during catheter operation. However, in a conventional application of this side-by-side construction, hemodialysis efficiency is greatly reduced, since the mouth of the return line is no longer disposed distal to the mouth of the suction line, and hence there is a much higher likelihood that cleansed blood exiting the return line will be immediately drawn back into the suction line of the dialysis catheter, thereby resulting in the undesirable recirculation problem discussed above. Furthermore, where the mouths of the two lines are disposed in a side-by-side configuration such as that shown in FIG. 3, suction from the suction line may cause the distal tip of the hemodialysis catheter to adhere to a vascular wall (see, for example, FIG. 4), which can also greatly reduce catheter efficiency. In order to reduce the possibility of, and/or in order to reduce the effects of, such suction adhesion to an adjacent vascular wall, some hemodialysis catheters provide small holes in the sides of the catheter, proximal to the catheter tip. Such side holes can permit blood flow to continue even where suction causes the distal end of the catheter to adhere to an adjacent vascular wall. However, since these side holes are smaller in size than the mouth of the suction line, they are incapable of supporting normal catheter flow rates and hence catheter flow rates are still greatly reduced.

Prior art hemodialysis catheters also tend to suffer from various additional deficiencies. By way of example but not limitation, even with the use of catheter lock solutions between dialysis sessions, blood clots may form in the mouths of one or both lumens of the hemodialysis catheter, and at locations between the mouths of the two lumens. This is particularly true during the time between dialysis sessions, when the hemodialysis catheter is not in active use. This is because the distal end of the hemodialysis catheter is disposed in a turbulent blood environment, and some of the catheter lock solution inevitably leaks out of the distal end of the hemodialysis catheter and is replaced by blood, which can then clot at the distal end of the hemodialysis catheter. These blood clots can be difficult and/or time-consuming to remove, thereby slowing down dialysis set-up and/or reducing dialysis throughput. In this respect it should be appreciated that blood clot removal can be particularly difficult where side windows are formed adjacent to the distal ends of the lumens of the hemodialysis catheter, since portions of the blood clots may extend through the windows and thereby mechanically "lock" the blood clots to the hemodialysis catheter.

Therefore, it would be desirable to provide a new hemodialysis catheter which is configured to minimize the aforementioned undesirable recirculation of dialyzed blood, yet which allows its lumens to be interchangeably used for suction or return functions. It would also be desirable to provide a new hemodialysis catheter which minimizes the possibility of the catheter inadvertently adhering to vascular walls, and which simplifies removing any clots which might form adjacent to the distal end of the catheter. And it would be desirable to provide a new hemodialysis catheter which is easy to manufacture and inexpensive to produce.

SUMMARY OF THE INVENTION

The present invention provides a novel method and apparatus for the dialysis of blood. Among other things, the present invention comprises the provision and use of a novel hemodialysis catheter which is configured to minimize the aforementioned undesirable recirculation of dialyzed blood, yet which allows its lumens to be interchangeably used for suction or return functions. The novel hemodialysis catheter is also designed to minimize the possibility of the catheter inadvertently adhering to vascular walls, and to simplify removal of any clots which might form adjacent to the distal end of the catheter. And the novel hemodialysis catheter is easy to manufacture and inexpensive to produce.

In one form of the invention, there is provided apparatus for use in dialyzing a patient, the apparatus comprising:

a hemodialysis catheter comprising:

an elongated body having a proximal end and a distal end, wherein the distal end terminates in a substantially planar distal end surface;

first and second lumens extending from the proximal end of the elongated body to the distal end of the elongated body, wherein the first and second lumens terminate on the substantially planar distal end surface in first and second mouths, respectively, arranged in side-by-side configuration, and further wherein the first and second lumens are separated by a septum; and first and second longitudinal slots formed in the distal end of the elongated body and communicating with the interiors of the first and second lumens, respectively, the first and second longitudinal slots opening on the substantially planar distal end surface;

wherein the first and second longitudinal slots each has a length and a width, relative to the dimensions of the first and second lumens and the rate of blood flow to be passed through the hemodialysis catheter, such that (i) when a given lumen is to be used for a return function, the primary blood flow will exit the mouth of that lumen, and (ii) when a given lumen is to be used for a suction function, the primary blood flow will enter the proximal end of the longitudinal slot associated with that lumen, whereby to minimize undesirable recirculation of dialyzed blood.

In one preferred form of the invention, where the dialysis flow rate is between about 350 mL/minute and 500 mL/minute, and where the suction (vacuum) prepump pressure is not more negative than about −250 mm/Hg and the return pressure does not exceed about 250 mm/Hg, and where the suction line and the return line both have D-shaped cross-sections with a longer dimension of about 3.5 mm and a shorter dimension of about 1.5 mm, the first and second longitudinal slots preferably have a slot width of about 0.065-0.100 inches, and a slot length of greater than 5 mm, with a slot length of 10 mm being preferred. In this respect it should be appreciated that an appropriate slot width is important to allow sufficient flow rates at acceptable pressure gradients, and an appropriate slot length is important to minimize recirculation.

In another form of the invention, there is provided apparatus for use in dialyzing a patient, the apparatus comprising:
 a hemodialysis catheter system comprising:
  a first elongated body having a proximal end and a distal end, wherein the distal end terminates in a first substantially planar distal end surface;
  a first lumen extending from the proximal end of the first elongated body to the distal end of the first elongated body, wherein the first lumen terminates on the first substantially planar distal end surface in a first mouth;
  a first longitudinal slot formed in the distal end of the first elongated body and communicating with the interior of the first lumen, the first longitudinal slot opening on the first substantially planar distal end surface;
  a second elongated body having a proximal end and a distal end, wherein the distal end terminates in a second substantially planar distal end surface;
  a second lumen extending from the proximal end of the second elongated body to the distal end of the second elongated body, wherein the second lumen terminates on the second substantially planar distal end surface in a second mouth;
  a second longitudinal slot formed in the distal end of the second elongated body and communicating with the interior of the second lumen, the second longitudinal slot opening on the second substantially planar distal end surface;
  wherein the first and second longitudinal slots each has a length and a width, relative to the dimensions of the first and second lumens and the rate of blood flow to be passed through the hemodialysis catheter system, such that (i) when a given lumen is to be used for a return function, the primary blood flow will exit the mouth of that lumen, and (ii) when a given lumen is to be used for a suction function, the primary blood flow will enter the proximal end of the longitudinal slot associated with that lumen, whereby to minimize undesirable recirculation of dialyzed blood.

In another form of the invention, there is provided a method for dialyzing the blood of a patient, the method comprising:
 providing apparatus for use in dialyzing a patient, the apparatus comprising:
  a hemodialysis catheter comprising:
   an elongated body having a proximal end and a distal end, wherein the distal end terminates in a substantially planar distal end surface;
   first and second lumens extending from the proximal end of the elongated body to the distal end of the elongated body, wherein the first and second lumens terminate on the substantially planar distal end surface in first and second mouths, respectively, arranged in side-by-side configuration, and further wherein the first and second lumens are separated by a septum; and
   first and second longitudinal slots formed in the distal end of the elongated body and communicating with the interiors of the first and second lumens, respectively, the first and second longitudinal slots opening on the substantially planar distal end surface;
   wherein the first and second longitudinal slots each has a length and a width, relative to the dimensions of the first and second lumens and the rate of blood flow to be passed through the hemodialysis catheter, such that (i) when a given lumen is to be used for a return function, the primary blood flow will exit the mouth of that lumen, and (ii) when a given lumen is to be used for a suction function, the primary blood flow will enter the proximal end of the longitudinal slot associated with that lumen, whereby to minimize undesirable recirculation of dialyzed blood;
 connecting the first lumen to the venous port of a dialysis machine, and connecting the second lumen to the arterial port of the dialysis machine; and
 withdrawing undialyzed blood from the body of a patient through the first lumen, and returning dialyzed blood to the body of a patient through the second lumen.

In another form of the invention, there is provided apparatus for use in withdrawing fluids from a patient and instilling fluids into a patient, the apparatus comprising:
 a catheter comprising:
  an elongated body having a proximal end and a distal end, wherein the distal end terminates in a substantially planar distal end surface;
  first and second lumens extending from the proximal end of the elongated body to the distal end of the elongated body, wherein the first and second lumens terminate on the substantially planar distal end surface in first and second mouths, respectively, arranged in side-by-side configuration, and further wherein the first and second lumens are separated by a septum; and
  first and second longitudinal slots formed in the distal end of the elongated body and communicating with the interiors of the first and second lumens, respectively, the first and second longitudinal slots opening on the substantially planar distal end surface;
  wherein the first and second longitudinal slots each has a length and a width, relative to the dimensions of the first and second lumens and the rate of fluid flow to be passed through the catheter, such that (i) when a given lumen is to be used for an instilling function, the primary fluid flow will exit the mouth of that lumen, and (ii) when a given lumen is to be used for a suction function, the primary fluid flow will enter the proximal end of the longitudinal slot associated with that lumen, whereby to minimize undesirable recirculation of fluid.

In another form of the invention, there is provided apparatus for use in withdrawing fluids from a patient and instilling fluids into a patient, the apparatus comprising:

a catheter system comprising:

a first elongated body having a proximal end and a distal end, wherein the distal end terminates in a first substantially planar distal end surface;

a first lumen extending from the proximal end of the first elongated body to the distal end of the first elongated body, wherein the first lumen terminates on the first substantially planar distal end surface in a first mouth;

a first longitudinal slot formed in the distal end of the first elongated body and communicating with the interior of the first lumen, the first longitudinal slot opening on the first substantially planar distal end surface;

a second elongated body having a proximal end and a distal end, wherein the distal end terminates in a second substantially planar distal end surface;

a second lumen extending from the proximal end of the second elongated body to the distal end of the second elongated body, wherein the second lumen terminates on the second substantially planar distal end surface in a second mouth;

a second longitudinal slot formed in the distal end of the second elongated body and communicating with the interior of the second lumen, the second longitudinal slot opening on the second substantially planar distal end surface;

wherein the first and second longitudinal slots each has a length and a width, relative to the dimensions of the first and second lumens and the rate of fluid flow to be passed through the catheter system, such that (i) when a given lumen is to be used for an instilling function, the primary fluid flow will exit the mouth of that lumen, and (ii) when a given lumen is to be used for a suction function, the primary fluid flow will enter the proximal end of the longitudinal slot associated with that lumen, whereby to minimize undesirable recirculation of fluid.

In another form of the invention, there is provided a method for withdrawing fluids from a patient and instilling fluids into a patient, the method comprising:

providing apparatus for use in withdrawing fluids from a patient and instilling fluids into a patient, the apparatus comprising:

a catheter comprising:

an elongated body having a proximal end and a distal end, wherein the distal end terminates in a substantially planar distal end surface;

first and second lumens extending from the proximal end of the elongated body to the distal end of the elongated body, wherein the first and second lumens terminate on the substantially planar distal end surface in first and second mouths, respectively, arranged in side-by-side configuration, and further wherein the first and second lumens are separated by a septum; and first and second longitudinal slots formed in the distal end of the elongated body and communicating with the interiors of the first and second lumens, respectively, the first and second longitudinal slots opening on the substantially planar distal end surface;

wherein the first and second longitudinal slots each has a length and a width, relative to the dimensions of the first and second lumens and the rate of fluid flow to be passed through the catheter, such that (i) when a given lumen is to be used for an instilling function, the primary fluid flow will exit the mouth of that lumen, and (ii) when a given lumen is to be used for a suction function, the primary fluid flow will enter the proximal end of the longitudinal slot associated with that lumen, whereby to minimize undesirable recirculation of fluid;

connecting the first lumen to a source of suction, and connecting the second lumen to a source of fluid; and withdrawing fluid from the body of a patient through the first lumen, and instilling fluid into the body of a patient through the second lumen.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 10-16 are schematic views showing how blood flow into, and out of, the novel hemodialysis catheter of FIGS. 5 and 6 minimizes recirculation;

FIG. 36 is a schematic view showing two single-lumen hemodialysis catheters also formed in accordance with the present invention;

DETAILED DESCRIPTION OF THE PREFERRED EMBODIMENTS

Figure 1:
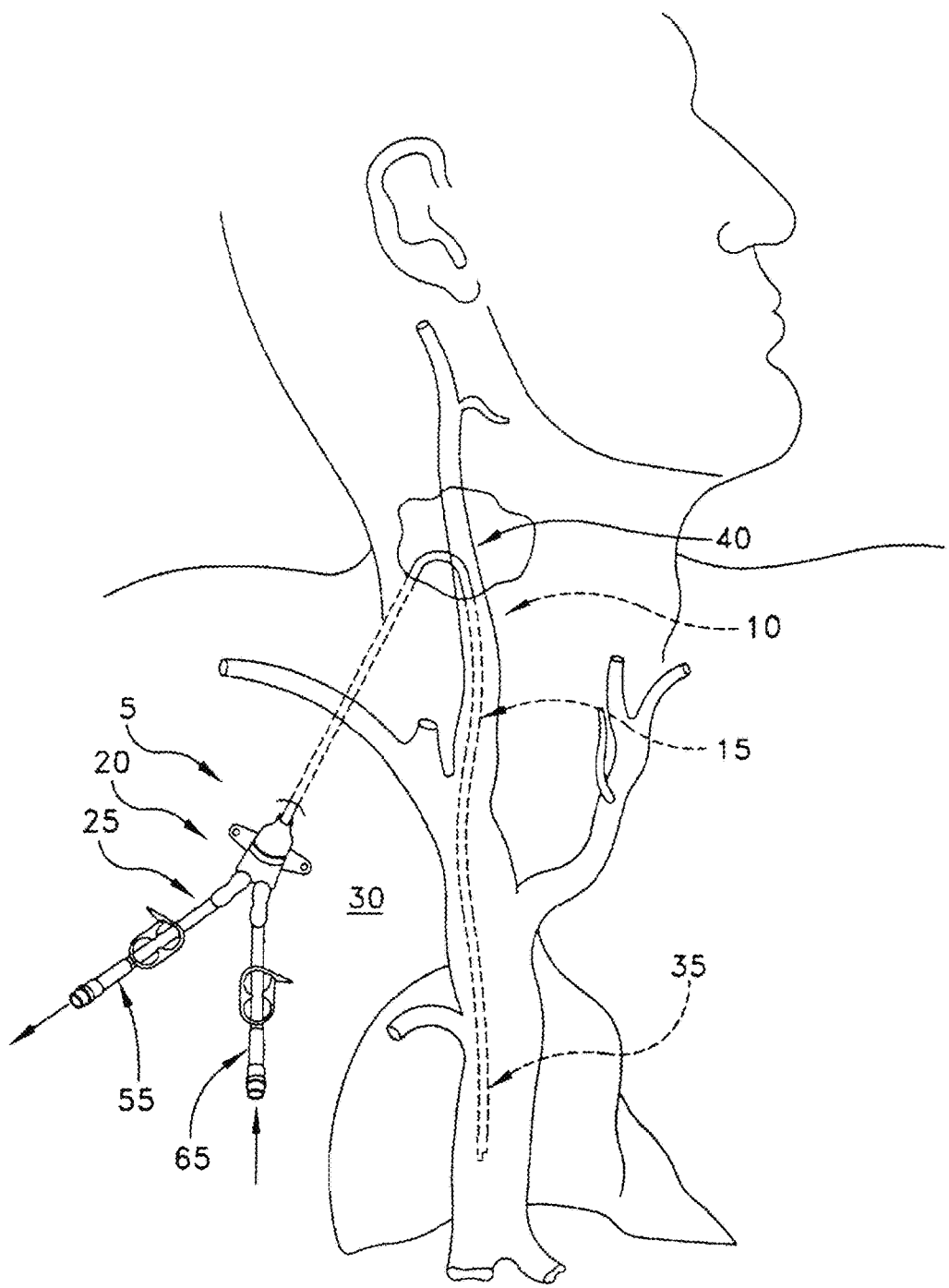
FIGS. 1 and 2 are schematic views showing one prior art hemodialysis catheter disposed in the body of a patient.
Figure 2:
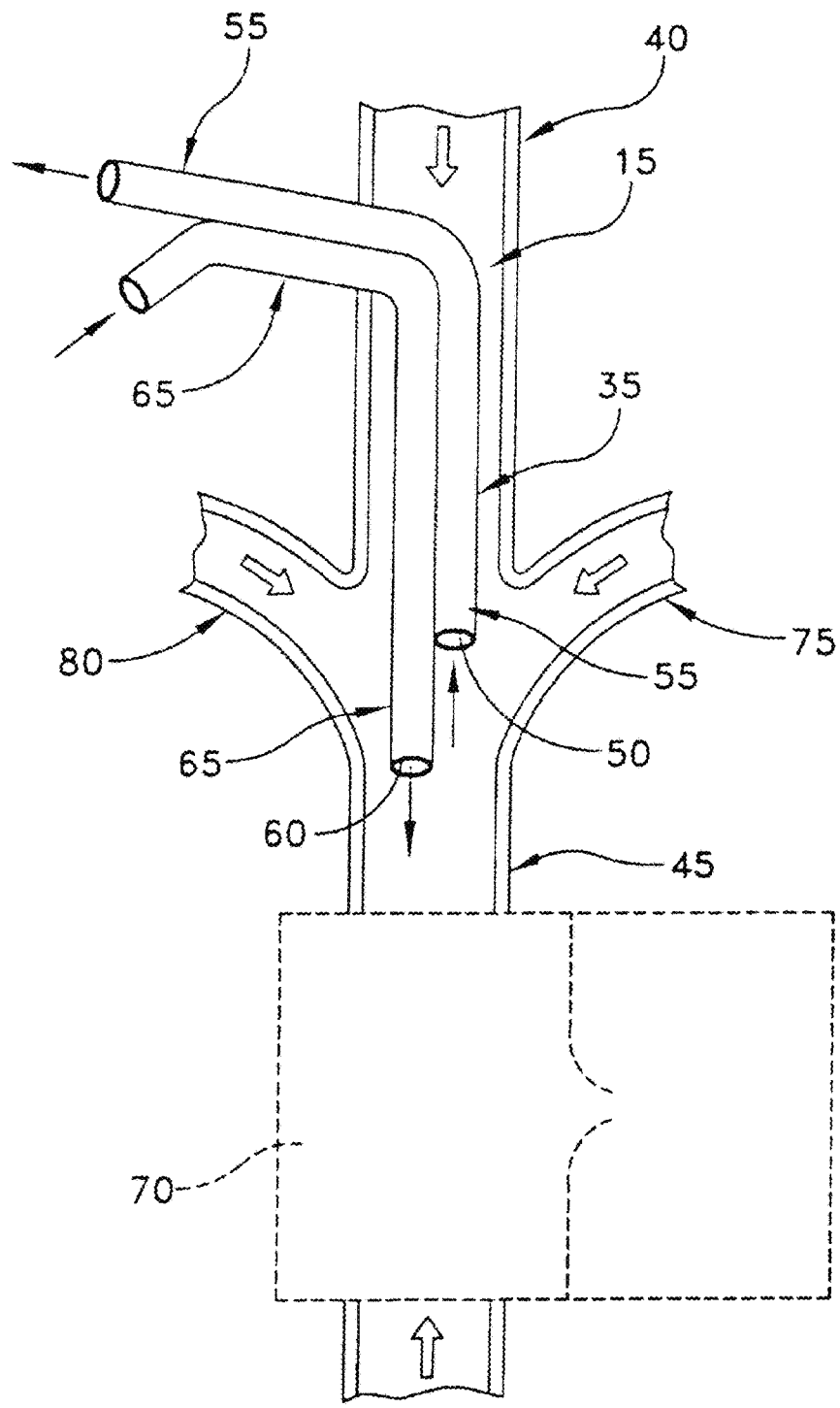
Figure 3:
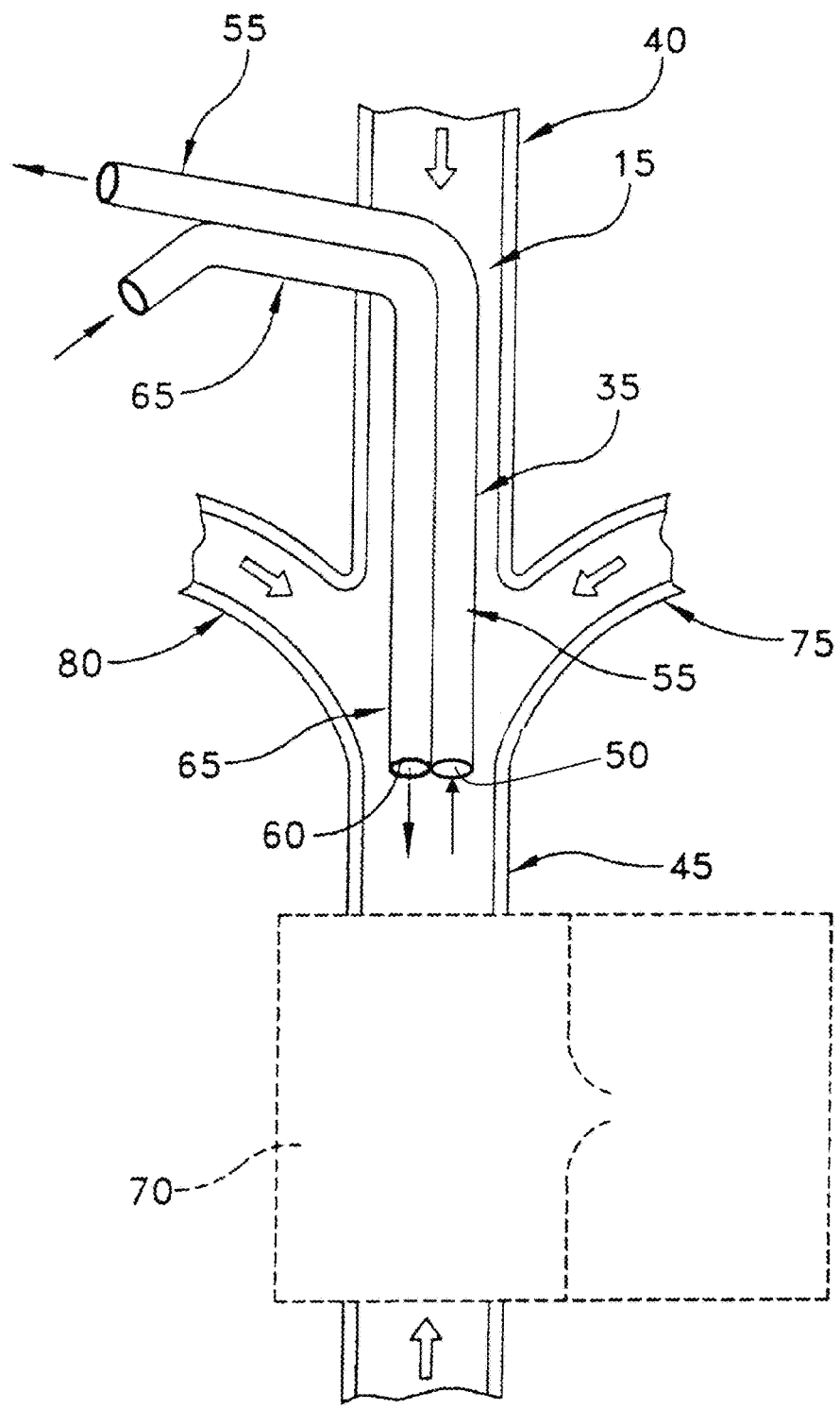
FIG. 3 is a schematic view showing another prior art hemodialysis catheter disposed in the body of a patient.
Figure 4:
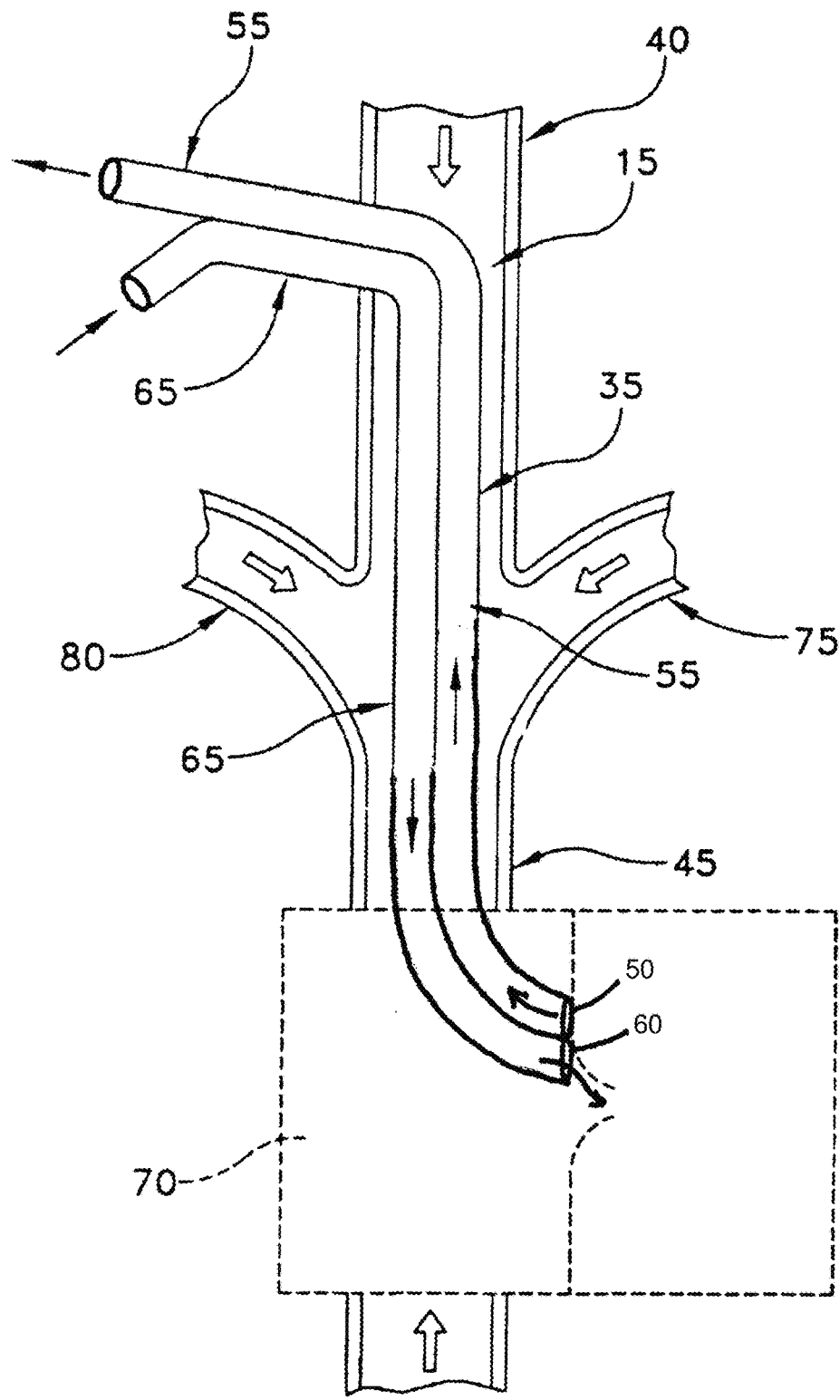
FIG. 4 is a schematic view showing the prior art hemodialysis catheter of FIG. 3 adhering to vascular tissue.
Figure 5:
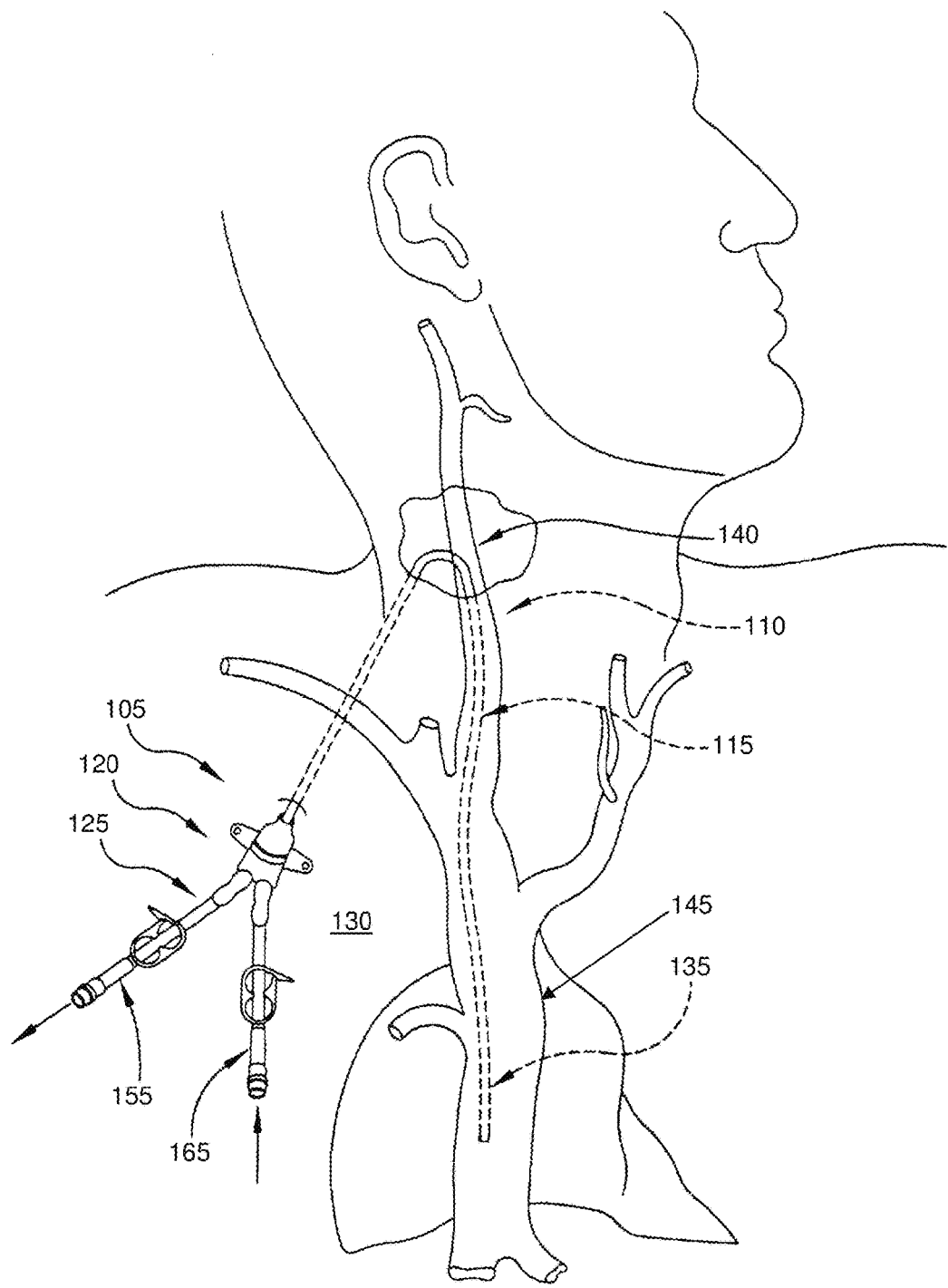
FIGS. 5 and 6 are schematic views showing a novel hemodialysis catheter formed in accordance with the present invention.
Figure 6:
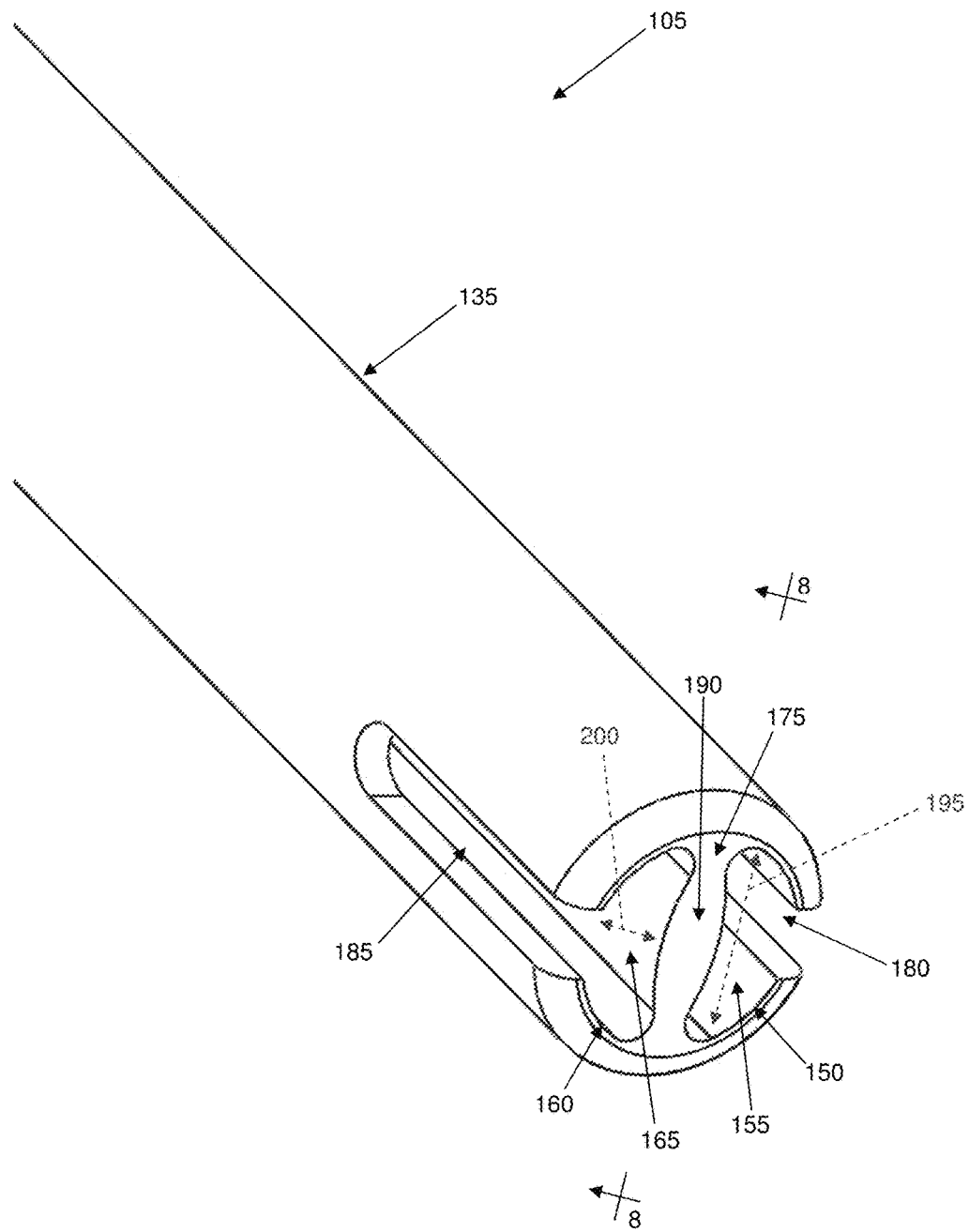
Figure 7:
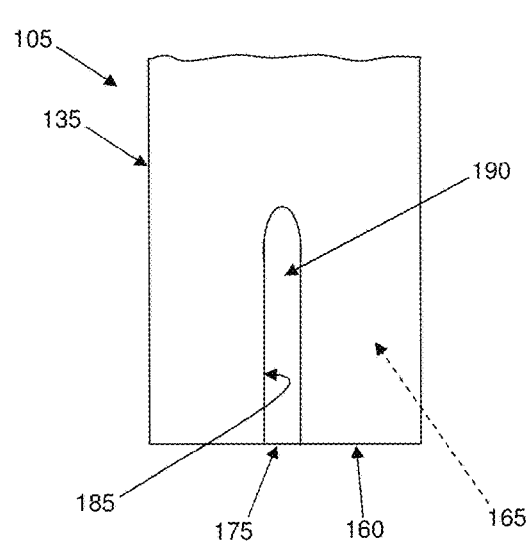
FIGS. 7 and 8 are schematic views (not necessarily to scale) showing the distal end of the novel hemodialysis catheter of FIGS. 5 and 6, with the views of FIGS. 7 and 8 being taken orthogonal to one another, and with FIG. 8 being a cross-sectional view taken along line 8-8 of FIG. 6.
Figure 8:
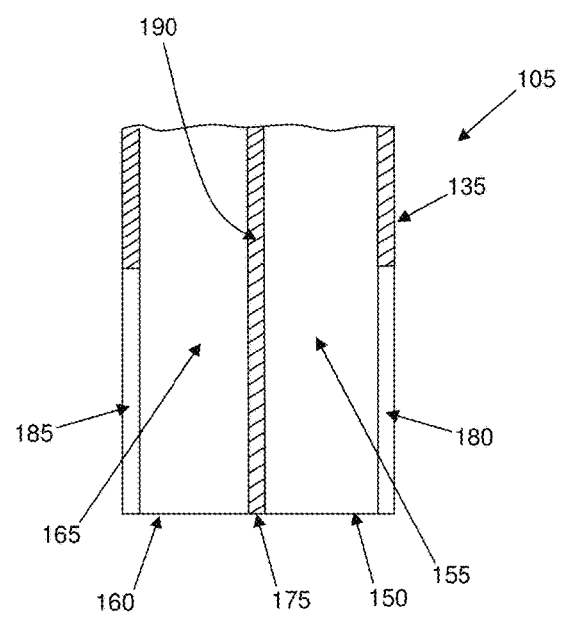

The present invention provides a novel method and apparatus for the dialysis of blood. Among other things, the present invention comprises the provision and use of a novel hemodialysis catheter which is configured to minimize the aforementioned undesirable recirculation of dialyzed blood, yet which allows its lumens to be interchangeably used for suction or return functions. The novel hemodialysis catheter of the present invention is also designed to minimize the possibility of the catheter inadvertently adhering to vascular walls, and to simplify removal of any clots which might form adjacent to the distal end of the catheter. And the novel hemodialysis catheter of the present invention is easy to manufacture and inexpensive to produce.

More particularly, and looking now at FIGS. 5-8, there is shown a novel hemodialysis catheter 105 which is intended for use in the dialysis of blood. Hemodialysis catheter 105 generally comprises a catheter portion 110 comprising a dual-lumen catheter element 115, and a connector portion 120 comprising an extracorporeal connector element 125. The catheter's extracorporeal connector element 125 is disposed against the chest 130 of the patient, with the distal end 135 of catheter element 115 extending down the patient's internal jugular vein 140 and into the patient's superior vena cava 145. More particularly, the distal end 135 of dual-lumen catheter element 115 is positioned within the patient's superior vena cava 145 such that the mouth 150 of a first lumen 155, and the mouth 160 of a second lumen 165, are both located between the patient's right atrium and the patient's left subclavia vein and right subclavia vein. Alternatively, the distal end 135 of dual-lumen catheter element 115 may be positioned so that mouth 150 of first lumen 155, and mouth 160 of second lumen 165, are located within the patient's right atrium. The hemodialysis catheter 105 is then left in this position relative to the body, waiting to be used during an active dialysis session.

Significantly, mouth 150 of first lumen 155 and mouth 160 of second lumen 165 are disposed in a side-by-side configuration, with the dual-lumen catheter element 115 terminating in a substantially flat distal end surface 175. Flat distal end surface 175 of dual-lumen catheter element 115 preferably extends substantially perpendicular to the longitudinal axes of first lumen 155 and second lumen 165. By disposing mouths 150 and 160 in the aforementioned side-by-side configuration, lumens 155 and 165 may be interchangeably used for suction or return applications, as will hereinafter be discussed.

Also significantly, a pair of longitudinal slots 180, 185 are formed in the side walls of distal end 135 of dual-lumen catheter element 115, with longitudinal slot 180 extending along and communicating with the interior of first lumen 155, and with longitudinal slot 185 extending along and communicating with the interior of second lumen 165. Preferably longitudinal slots 180, 185 extend at a right angle to the plane of the septum 190 which separates first lumen 155 from second lumen 165. By providing first lumen 155 and second lumen 165 with the aforementioned longitudinal slots 180, 185, respectively, the aforementioned undesirable recirculation of dialyzed blood is minimized, even though the mouths 150, 160 of the lumens 155, 165, respectively, are disposed in a side-by side configuration, as will hereinafter be discussed.

In one preferred form of the present invention, the distal end 135 of catheter element 115 has a substantially round outer surface (i.e., the distal end 135 of catheter element 115 has a substantially round cross-section), and first lumen 155 and second lumen 165 are each formed with a substantially D-shaped cross-section (FIG. 6), characterized by a longer dimension 195 and a shorter dimension 200.

When hemodialysis is to be performed on a patient, extracorporeal connector element 125 of hemodialysis catheter 105 is appropriately connected to a dialysis machine (not shown), e.g., first line 155 is connected to the suction port of the dialysis machine, and second line 165 is connected to the return port of the dialysis machine. In this case, first line 155 serves as the suction line and second line 165 serves as the return line. Alternatively, first line 155 is connected to the return port of the dialysis machine, and second line 165 is connected to the suction port of the dialysis machine. In this case, first line 155 serves as the return line and second line 165 serves as the suction line. It is a significant aspect of the present invention that the lumens of the hemodialysis catheter 105 are not dedicated to a particular function, i.e., either lumen may be used for suction function and either lumen may be used for return function.

For the purposes of the description which hereinafter follows, it will be assumed that first line 155 is connected to the suction port of the dialysis machine, and second line 165 is connected to the return port of the dialysis machine. In this case, first line 155 serves as the suction line to withdraw undialyzed blood from the patient and second line 165 serves as the return line to return dialyzed blood to the patient.

The dialysis machine is then activated (i.e., the dialysis machine's blood pump is turned on and the flow rate set), whereupon the dialysis machine will withdraw relatively "dirty" blood from the patient through suction line 155 and return relatively "clean" blood to the patient through return line 165.

Figure 9:
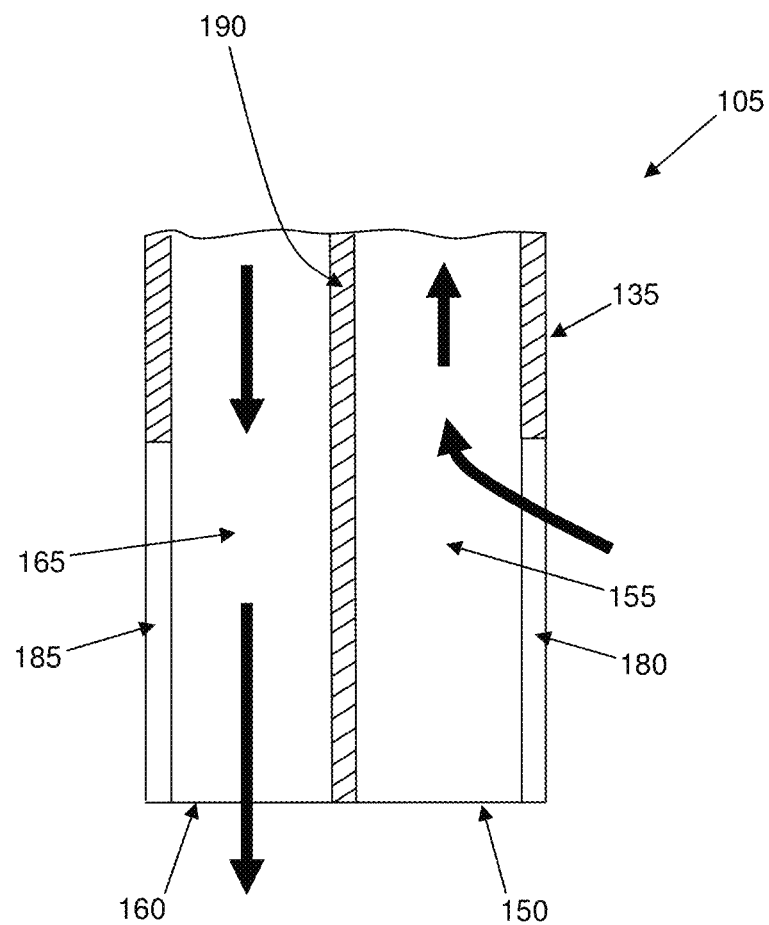
FIG. 9 is a schematic view (not necessarily to scale) showing the mode of operation of the novel hemodialysis catheter of FIGS. 5-8.
Figure 10:
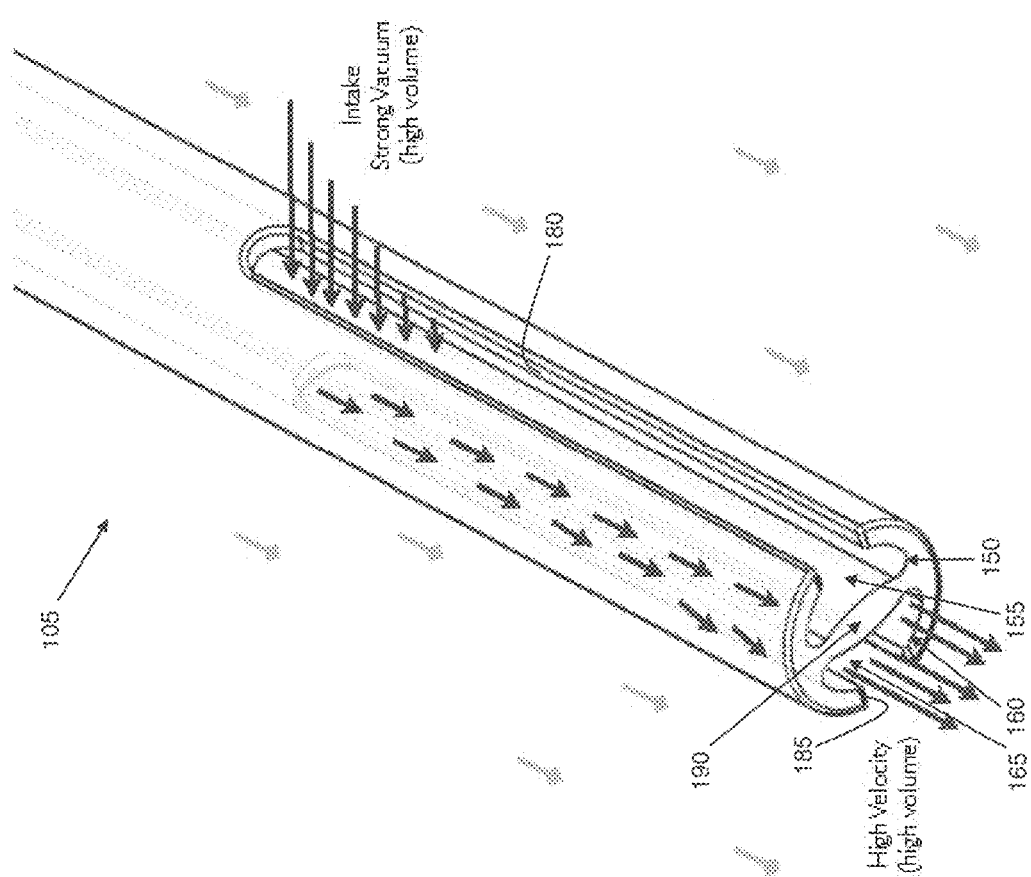
Figure 12:
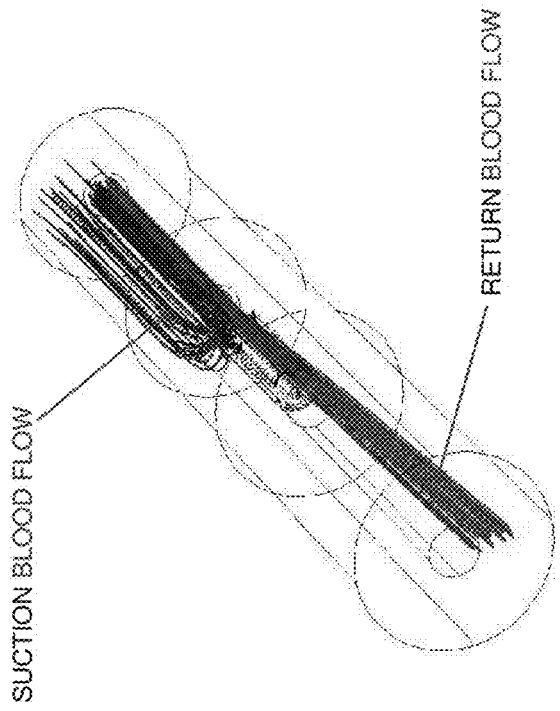
Figure 11:
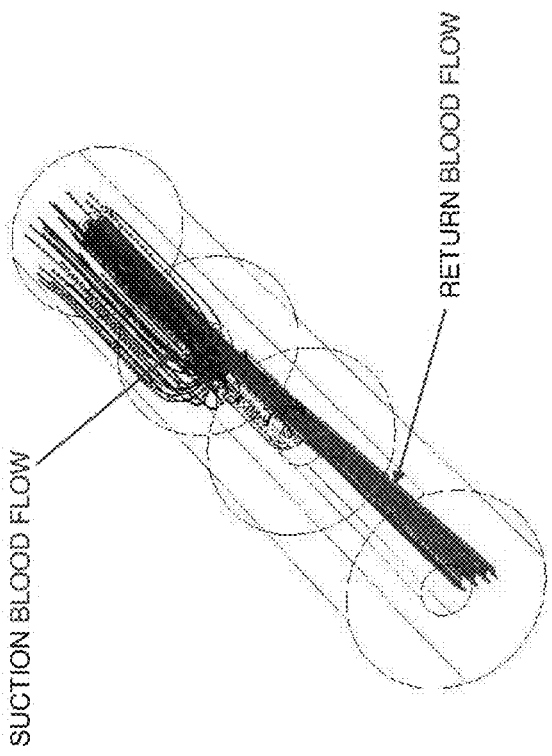
Figures 15, 16:
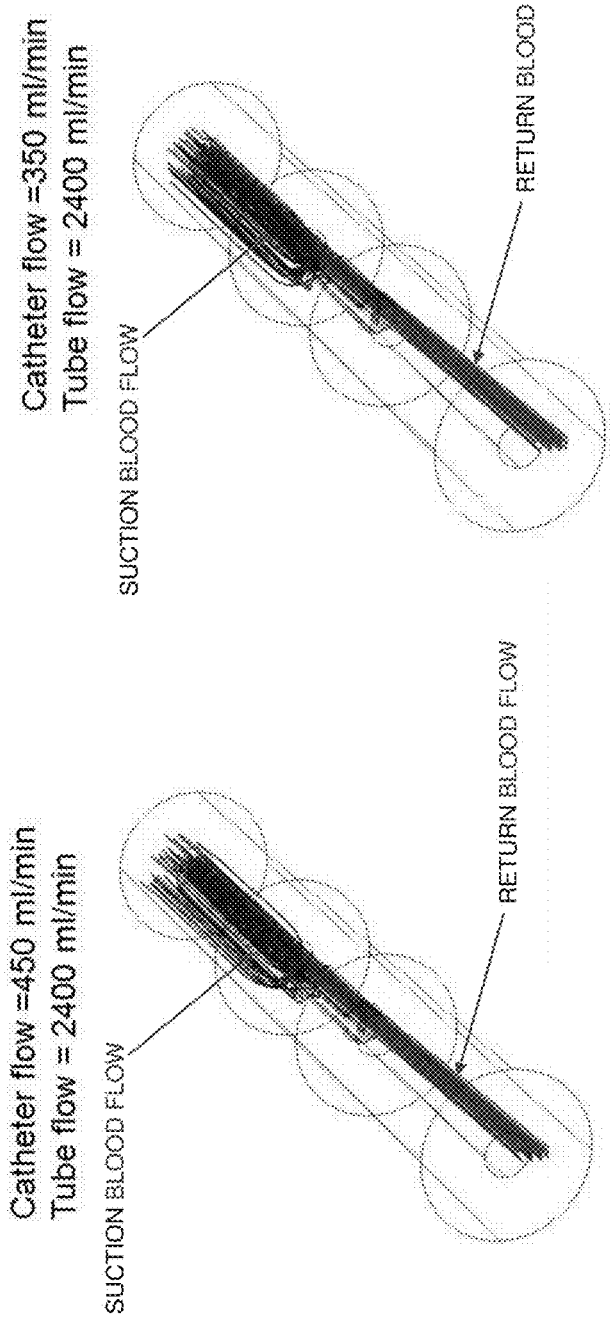
Figure 17:
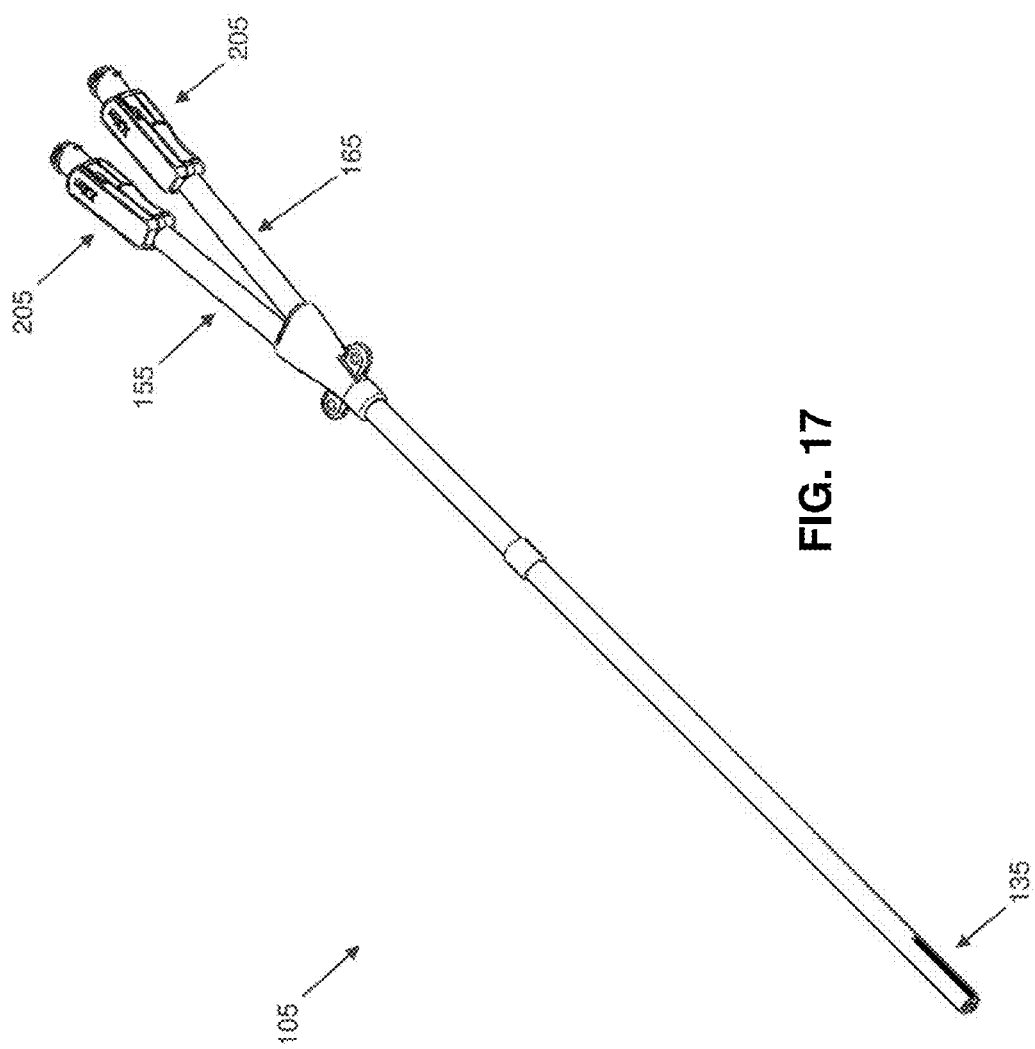
FIGS. 17-25 are schematic views showing how an open/close valve may be incorporated into one or both of the blood lines of the novel hemodialysis catheter of FIGS. 5 and 6 in order to facilitate flow control.
Figure 18:
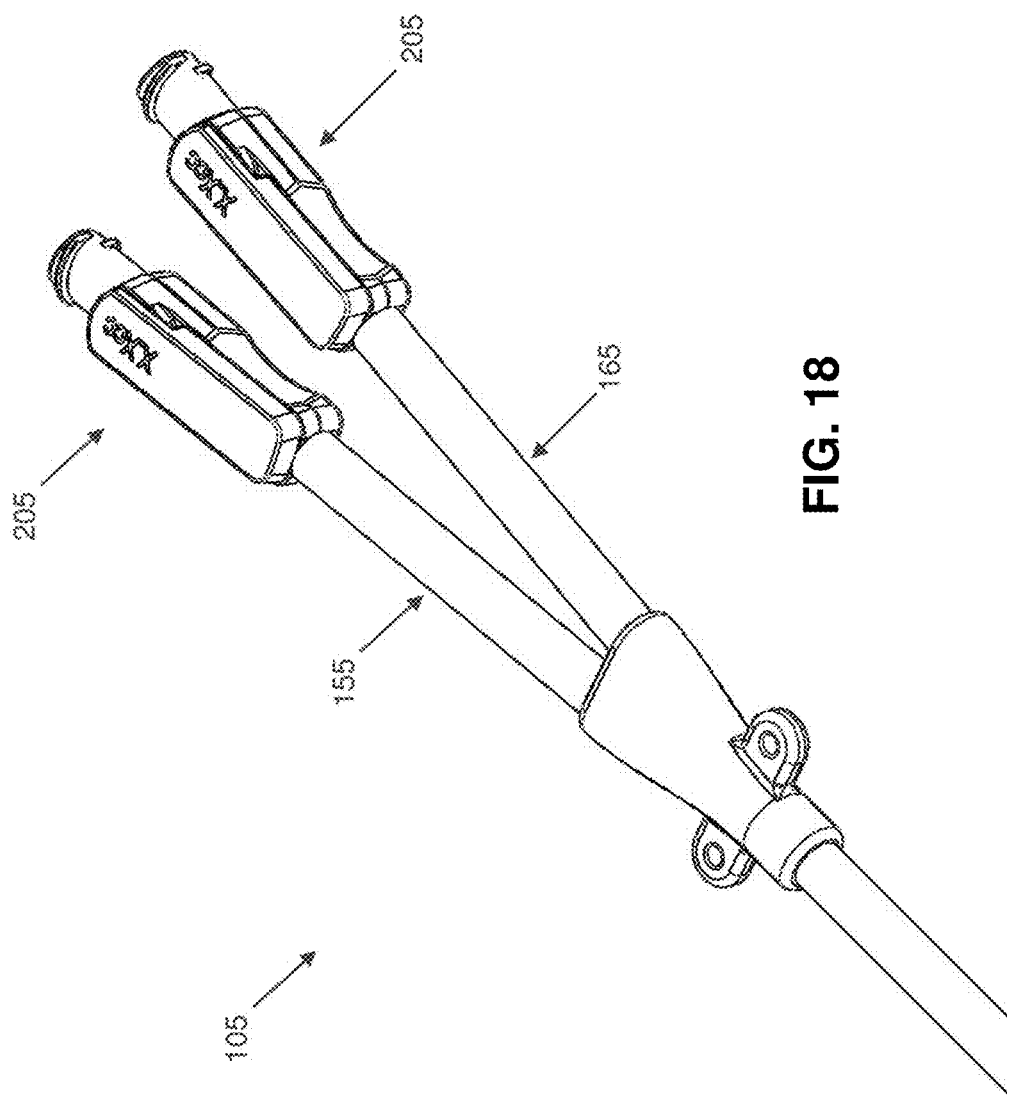
Figure 19:
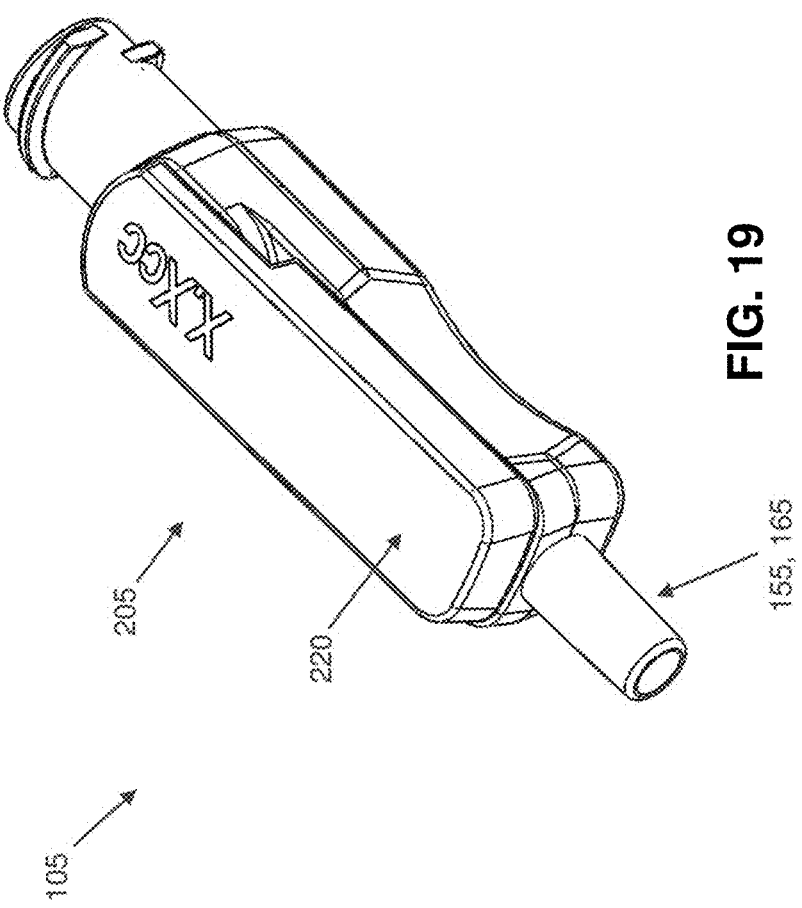
Figure 20:
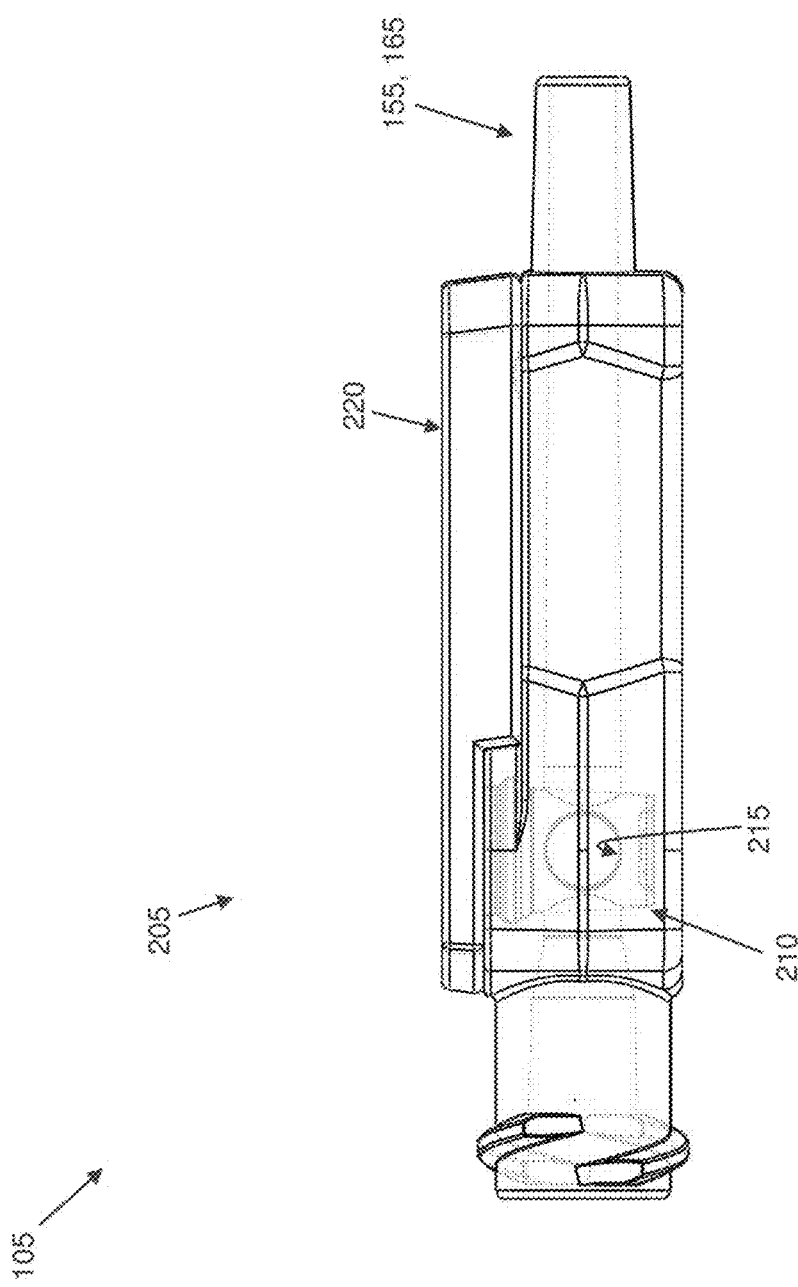
Figure 21:
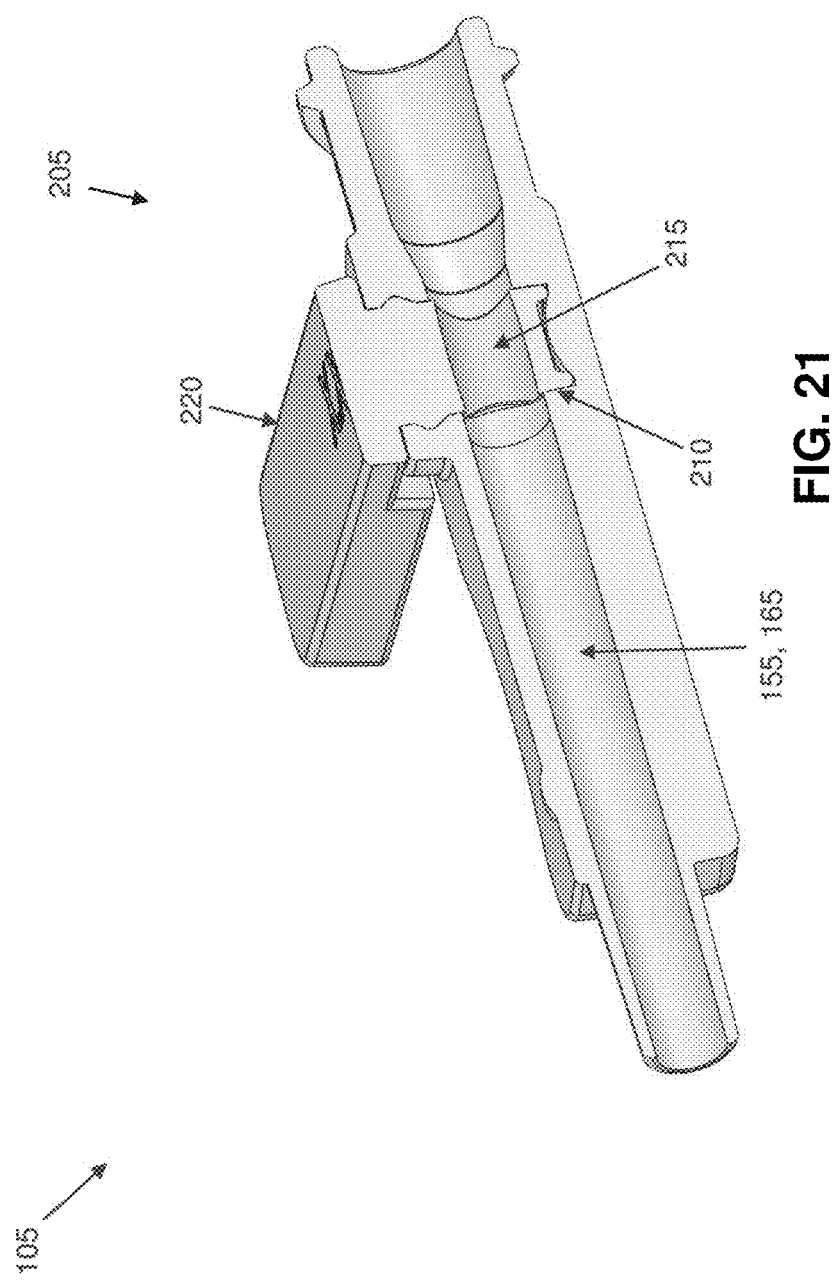
Figure 22:
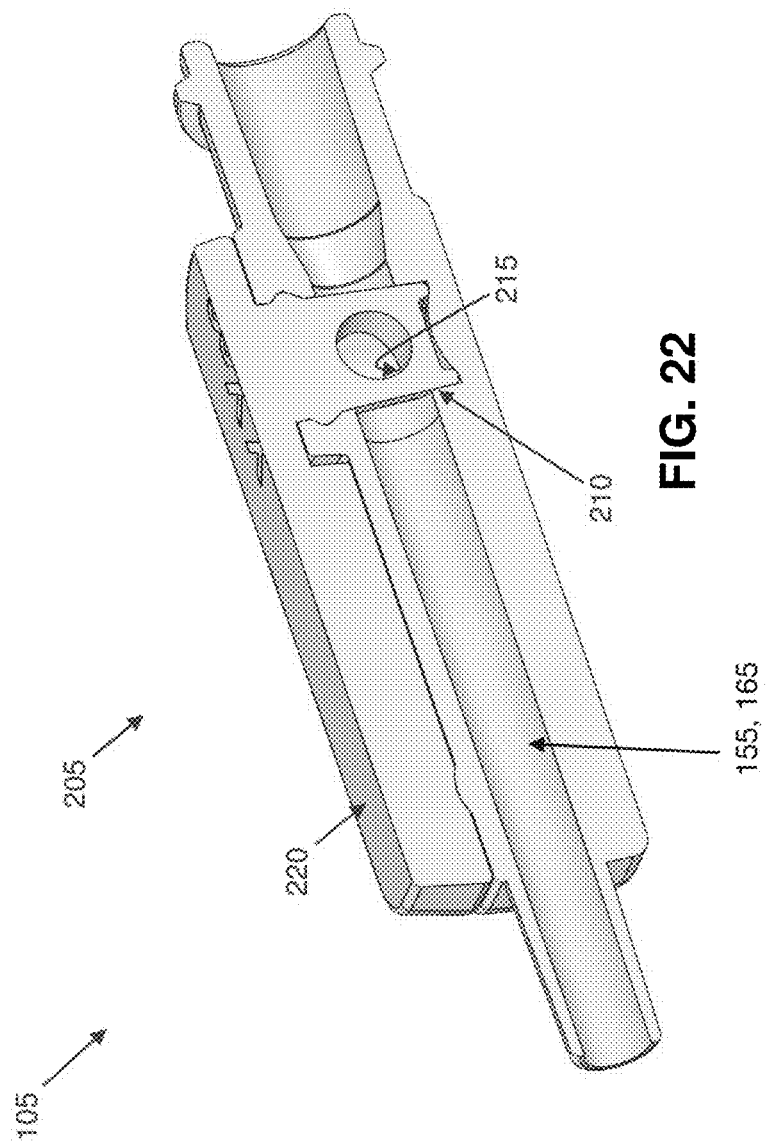
Figure 23:
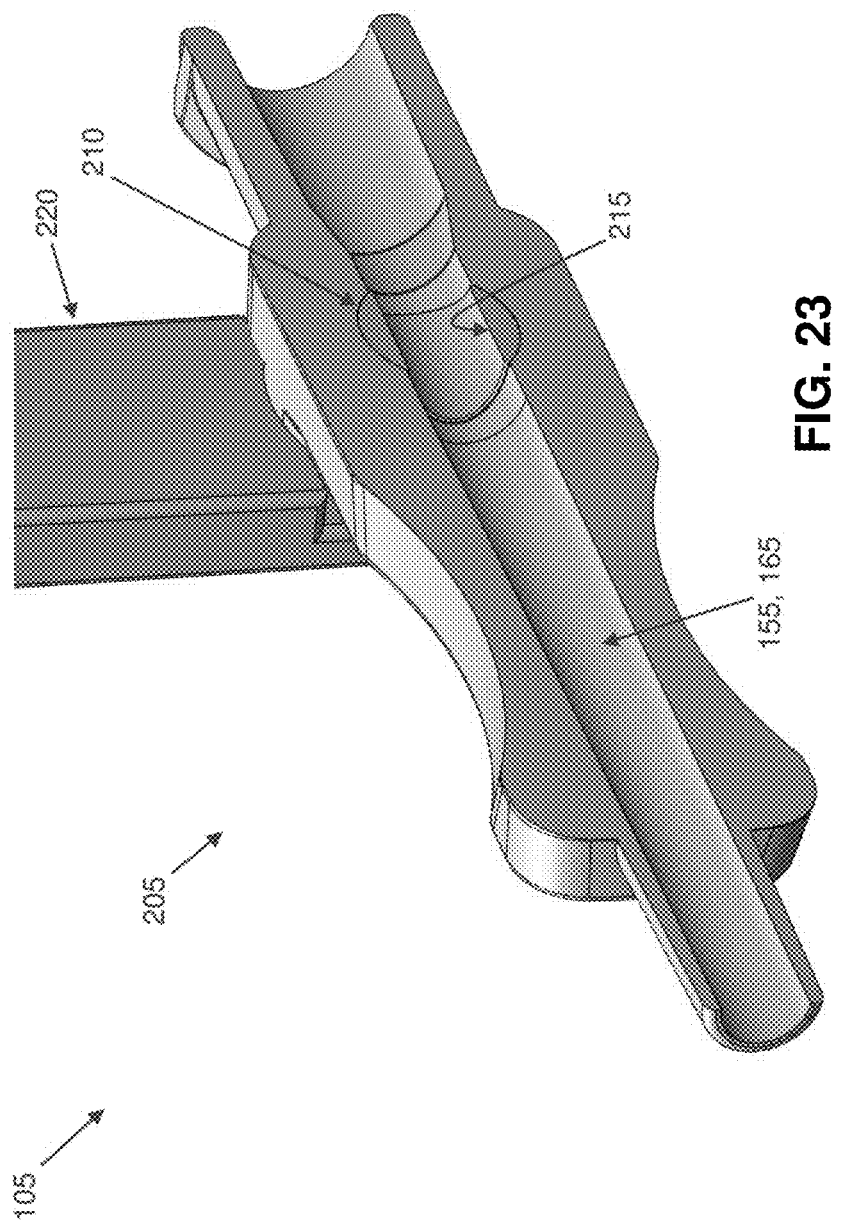
Figure 24:
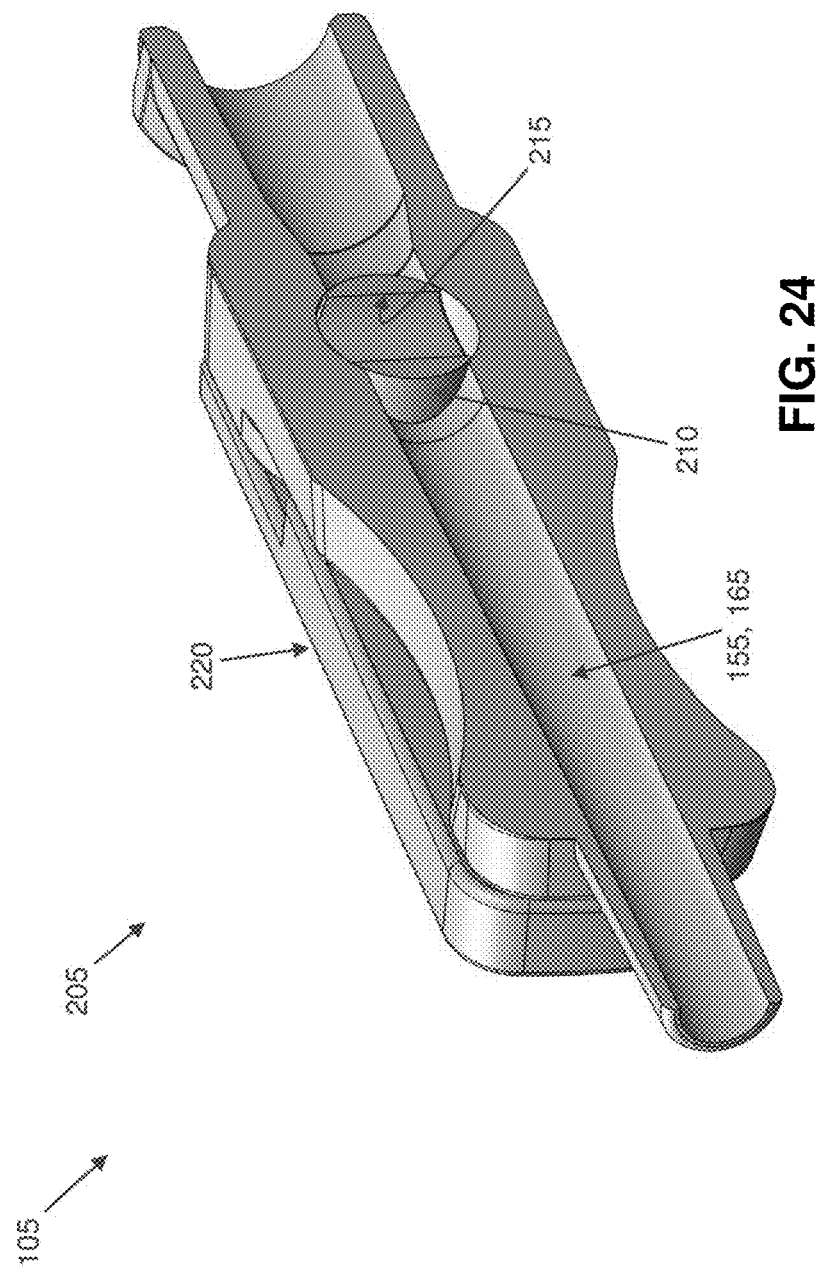
Figure 25:
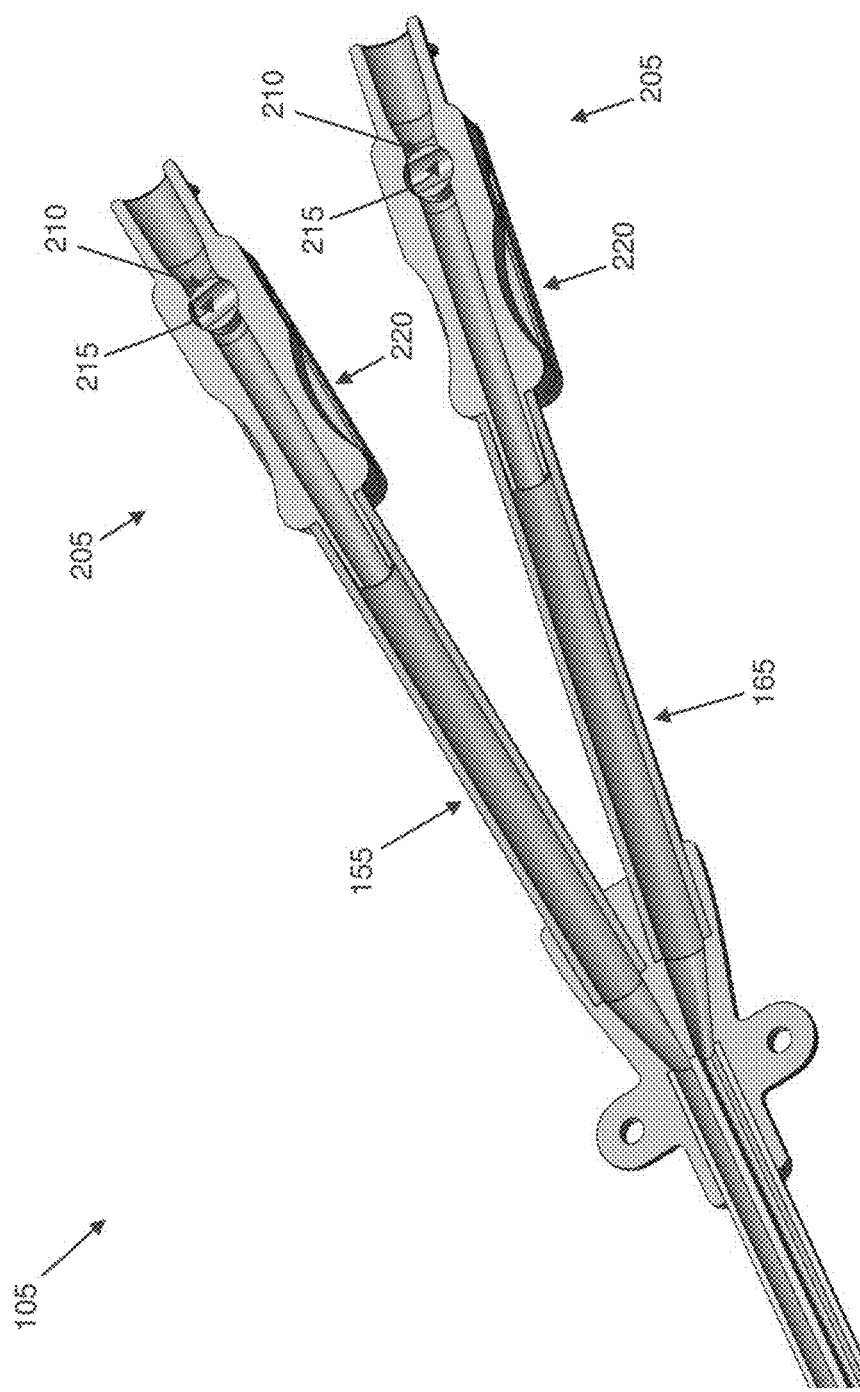

Significantly, with the novel hemodialysis catheter of the present invention, there is minimal undesirable recirculation of the undialyzed blood, even though mouth 150 of first lumen 155 (i.e., the mouth of the suction line) is disposed immediately adjacent to mouth 160 of second lumen 165 (i.e., the mouth of the return line) in a side-by-side relation. This is due to the novel provision of the aforementioned longitudinal slots 180, 185. More particularly, and looking now at FIGS. 9 and 10, longitudinal slots 180, 185 are configured such that the majority of the blood taken in by suction line 155 is admitted at the proximal end of longitudinal slot 180, where the level of suction is the greatest; and the majority of the blood discharged by return line 165 is ejected at the distal end of lumen 165, i.e., out mouth 160, since this is in direct line with the longitudinal axis of return line 165. As a result, there is minimal undesirable recirculation of the dialyzed blood, even though the mouths 150, 160 of lumens 155, 165, respectively, are disposed in side-by-side configuration. This result is ensured by forming longitudinal slots 180, 185 with the proper configuration (i.e., the proper length and width) relative to the dimensions of the hemodialysis catheter and the blood flow rates through the catheter.

More particularly, it has been discovered that, by controlling certain parameters of the hemodialysis system, the recirculation rate of the dual-lumen, flat-end hemodialysis catheter 105 can be minimized. These parameters include, but are not limited to, (i) the size of lumens 155, 165; (ii) the length and width of longitudinal slots 180, 185; (iii) the thickness of the side wall of hemodialysis catheter 105 at longitudinal slots 180, 185; and (iv) the rate of flow through hemodialysis catheter 105. Another factor affecting the rate of recirculation of hemodialysis catheter 105 is the rate of flow of the ambient blood surrounding hemodialysis catheter 105.

In general, it is preferred that longitudinal slots 180, 185 be sized so that greater than 85% of the flow out of the return line exits the distal mouth of that line, and so that greater than 85% of the flow into the suction line enters the proximal $1/3^{rd}$ of its associated longitudinal slot, and so that the hemodialysis catheter has a recirculation rate of less than 1%.

In general, it is also preferred that longitudinal slots 180, 185 have a length of between approximately 8 mm and 30 mm, since this length is long enough to adequately separate the inflow and outflow streams and thereby minimize recirculation, but short enough that the entire length of the longitudinal slots 180, 185 can fit within the right atrium of the heart. In addition, it has been found that by providing longitudinal slots 180, 185 with a length of between approximately 8 mm and 30 mm, the hemodialysis catheter will function with the desired minimal recirculation rate while minimizing loss of the catheter lock solution through longitudinal slots 180, 185.

In general, it is preferred that the lumens 155, 165 have a D-shaped configuration, and that the width of the longitudinal slots 180, 185 be between approximately 30% and 60% of the longer dimension 195 of the D-shaped lumen.

By way of example but not limitation, where the hemodialysis catheter 105 has a diameter of 15.5 French (i.e., 0.202 inch), where its lumens 155, 165 have a substantially D-shaped cross-section characterized by a longer dimension 195 of 3.5 mm (i.e., 0.14 inch) and a shorter dimension 200 of 1.5 mm (i.e., 0.060 inch), and where the flow rate of each lumen is to be set at 350-450 mL per minute, it is desirable that longitudinal slots 180, 185 have a length of 10 mm (i.e., 0.394 inch) and a width of 1.5 mm (i.e., 0.059 inch), whereby to produce a recirculation rate of less than 1%.

Among other things, it should be appreciated that an appropriate slot width is important to allow sufficient flow rates at acceptable pressure gradients, and an appropriate slot length is important to minimize recirculation. In this respect it will be appreciated that a wider slot and lower pressure gradients help minimize hemolysis.

FIGS. 11-16 illustrate experimental results confirming that, by providing lumens 155, 165 with appropriately-sized longitudinal slots 180, 185, recirculation can be effectively eliminated even where mouths 150, 160 of lumens 155, 165 are arranged in a side-by-side configuration.

In addition to the foregoing, it should also be appreciated that, even though the distal end of novel hemodialysis catheter 105 terminates in a flat distal end surface 175, with mouths 150 and 160 arranged in a side-by-side configuration, the construction of hemodialysis catheter 105 minimizes the possibility of the catheter inadvertently adhering to vascular walls. This is also due to the provision of the aforementioned longitudinal slots 180, 185. More particularly, with the hemodialysis catheter of the present invention, if the flat distal end surface 175 of the dialysis catheter should encounter a vascular wall, the longitudinal slot associated with the suction line will admit blood into the suction lumen, thereby keeping the distal end of the hemodialysis catheter from significantly adhering to the vascular wall. This happens because "suction forces" to adhere the catheter to the vascular wall cannot be maintained, since there are two openings (i.e., the slot opening and the distal end opening) and these two openings are spaced from one another and located 90° apart.

Also, if a blood clot should form at the distal end of hemodialysis catheter 105, e.g., during periods between dialysis sessions, the construction of the hemodialysis catheter makes it a simple matter to clear the blood clot from the distal end of the catheter. More particularly, inasmuch as the longitudinal slots 180, 185 extend all the way to the distal end of the hemodialysis catheter, any blood clots forming on the distal end of the hemodialysis catheter can be easily removed from the hemodialysis catheter by simply "blowing" the blood clots out the distal end of the hemodialysis catheter—there is no mechanical adhesion of the blood clot to the hemodialysis catheter, as there might be, for example, if the longitudinal slots 180, 185 were replaced by windows, in which case a portion of the blood clot might protrude through the window and mechanically "lock" the blood clot to the hemodialysis catheter.

And the hemodialysis catheter is exceedingly simple in design, making it easy to manufacture and inexpensive to produce.

Thus it will be seen that the present invention provides a novel hemodialysis catheter which is configured to minimize undesirable recirculation of dialyzed blood, yet which allows its lumens to be interchangeably used for suction or return functions. And the present invention provides a novel hemodialysis catheter that minimizes the possibility of the catheter inadvertently adhering to vascular walls, and which simplifies the removal of any clots which might form on the distal end of the catheter. And the present invention provides a novel hemodialysis catheter which is easy to manufacture and inexpensive to produce.

Blood Lines with Open/Close Valves

If desired, a novel open/close valve may be incorporated into each of the blood lines of novel hemodialysis catheter 105 in order to facilitate flow control through the blood line.

More particularly, in prior art hemodialysis catheters, clamps are applied to the suction and return lines at the proximal end of the hemodialysis catheter in order to close off flow when desired, e.g., when the hemodialysis catheter is not connected to a dialysis machine, etc. However, these clamps are essentially hose clamps which compress the suction and return lines of the hemodialysis catheter. This can cause damage to the suction and return lines, particularly over time. Furthermore, these clamps are bulky and present edges, which makes them uncomfortable for the patient. To this end, the present invention provides a novel open/closed valve which may be incorporated into each of the blood lines of the novel hemodialysis catheter in order to facilitate flow control through the blood line.

In one preferred form of the invention, and looking now at FIGS. 17-25, a valve 205 may be provided for each blood line 155, 165, where valve 205 comprises a cylinder 210 which extends across the lumen of the blood line. Cylinder 210 comprises a diametrically-extending through-hole 215 which may be aligned with, or set transverse to, the longitudinal axis of the flow path, so as to open up flow, or close off flow, respectively, through the flow path of the blood line. A handle 220 is attached to cylinder 210 so as to permit the user to adjust the rotational position of cylinder 210, and hence control flow through the blood line (preferably in either the "on" or "off" position).

Tunneling Tool

In practice, it is generally desirable to deploy a hemodialysis catheter so that the hemodialysis catheter enters a jugular vein of the patient and, furthermore, so that the hemodialysis catheter extends a distance under the skin before entering the jugular vein of the patient. This approach allows the access end of the hemodialysis catheter to exit the skin of the patient at the chest of the patient even as the working end of the hemodialysis catheter enters a jugular vein for direct passage down to the superior vena cava or the right atrium of the heart.

Figure 26:
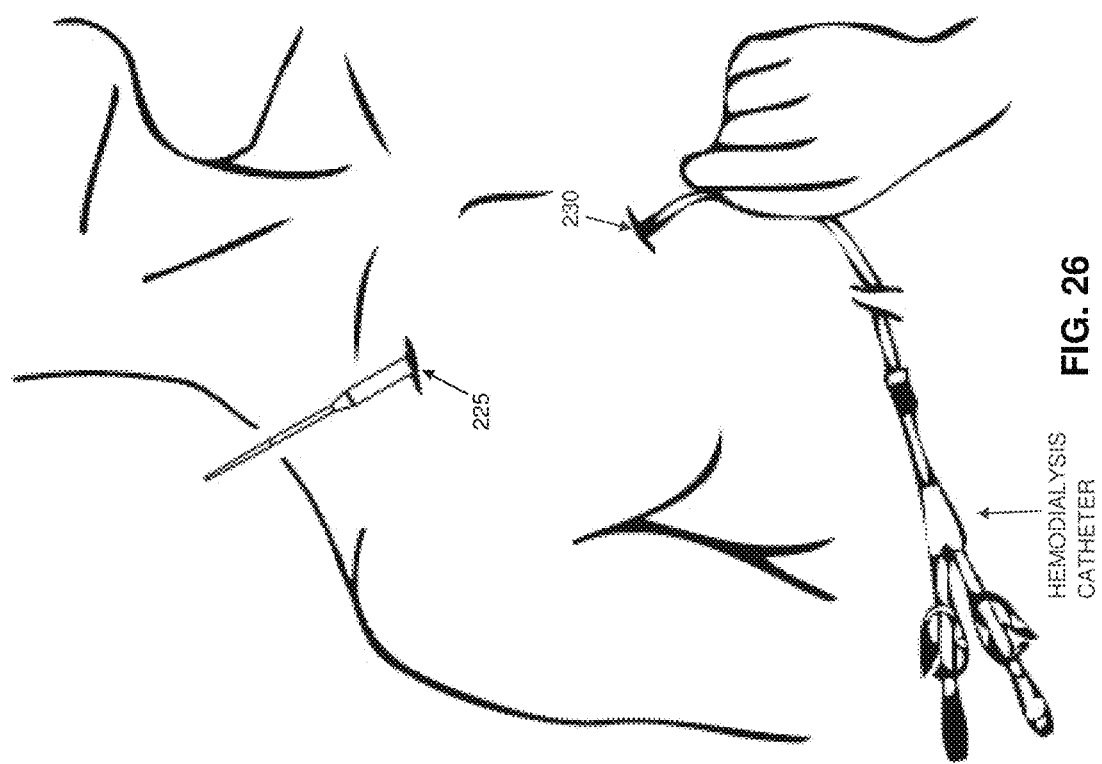
FIGS. 26-35 are schematic views showing a novel tunneling tool which may be used in connection with the novel hemodialysis catheter of FIGS. 5 and 6.
Figure 27:
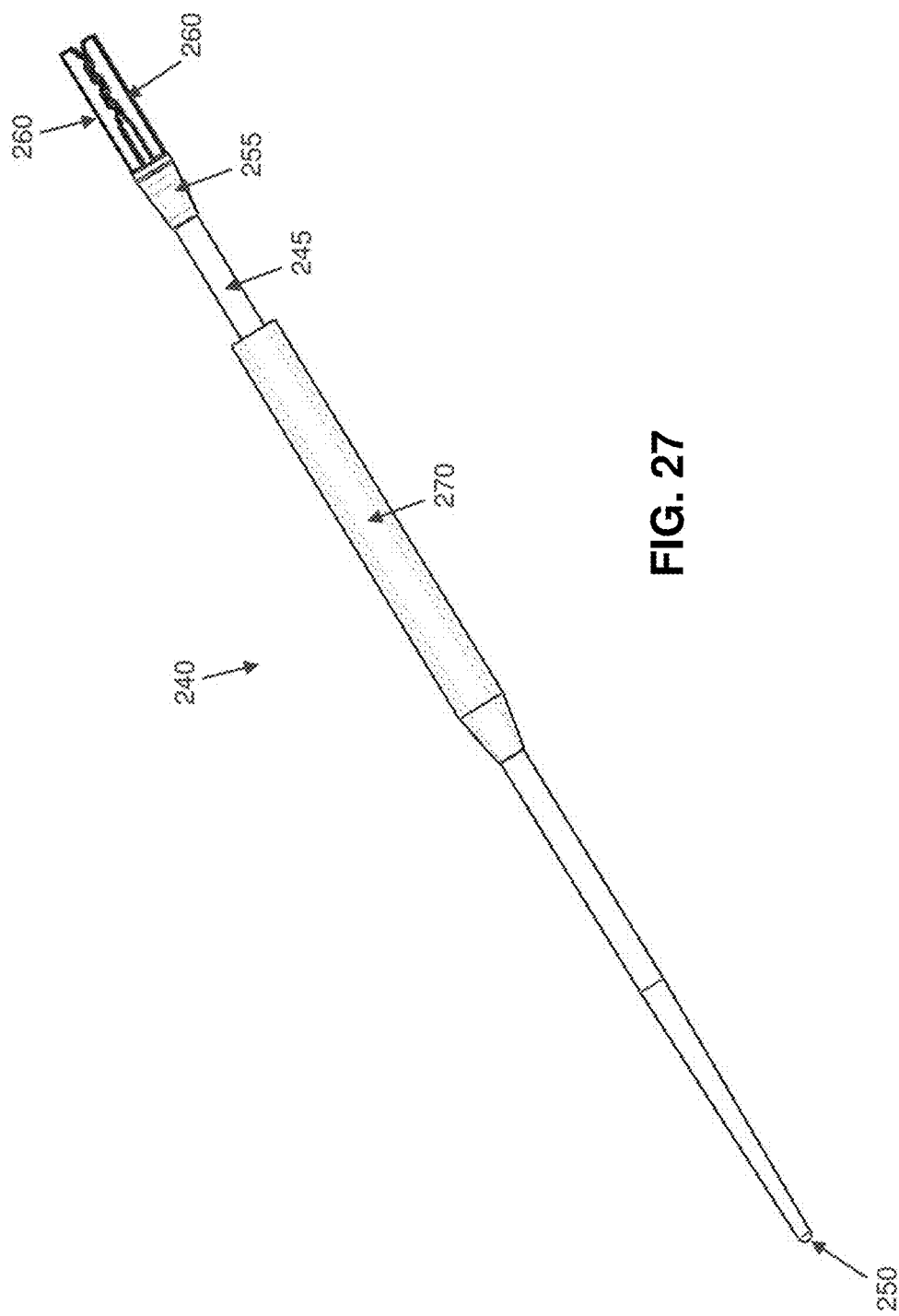
Figure 28:
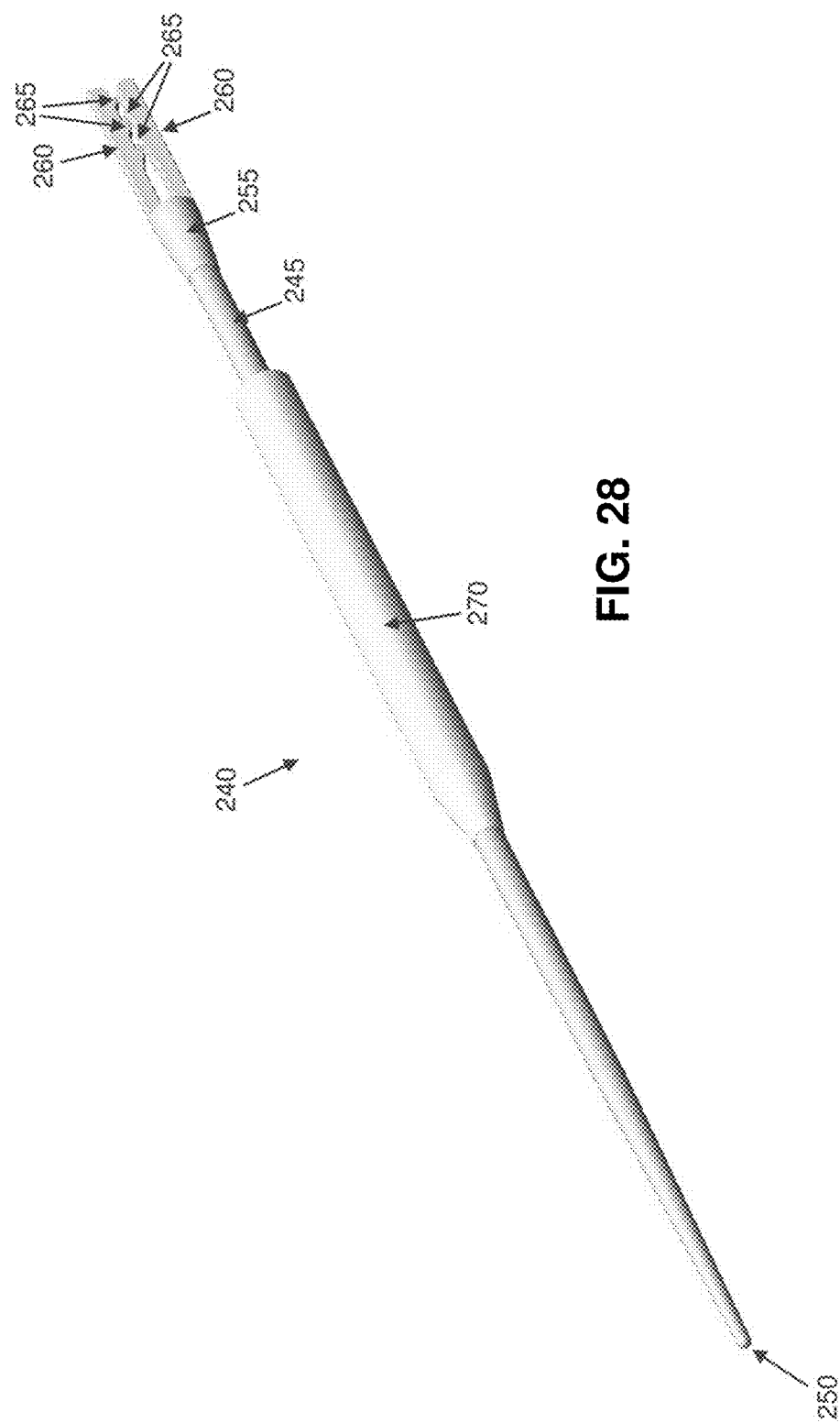
Figure 29:
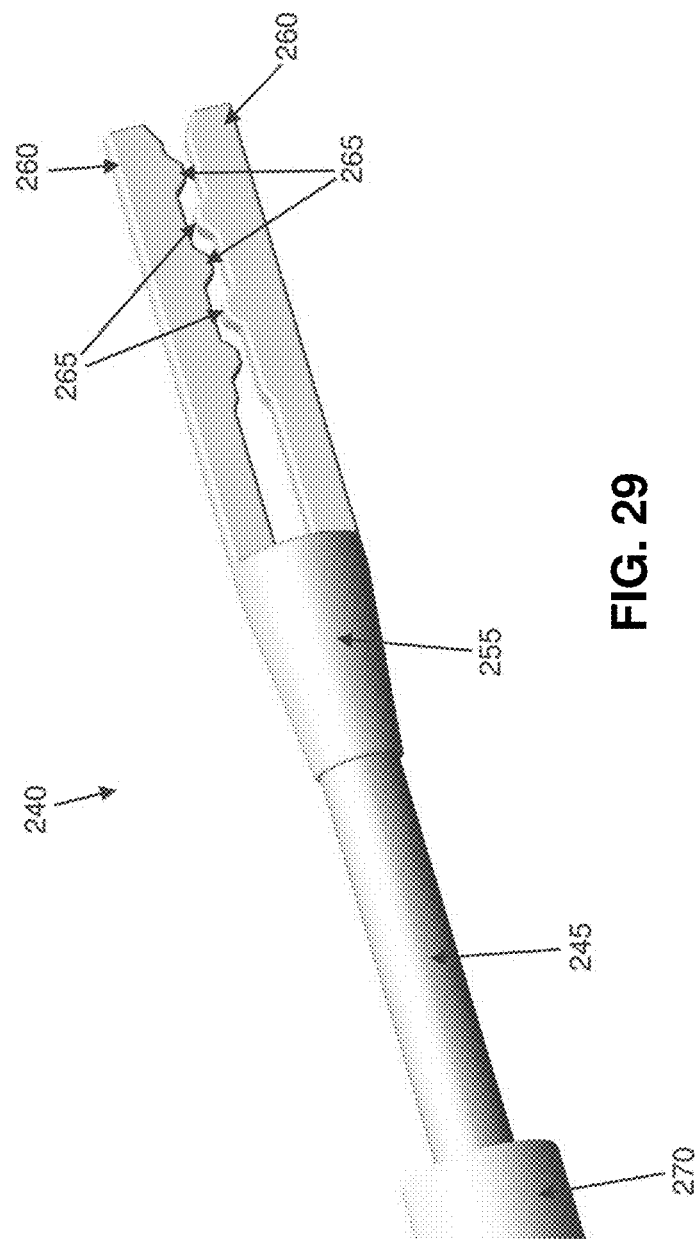
Figure 30:
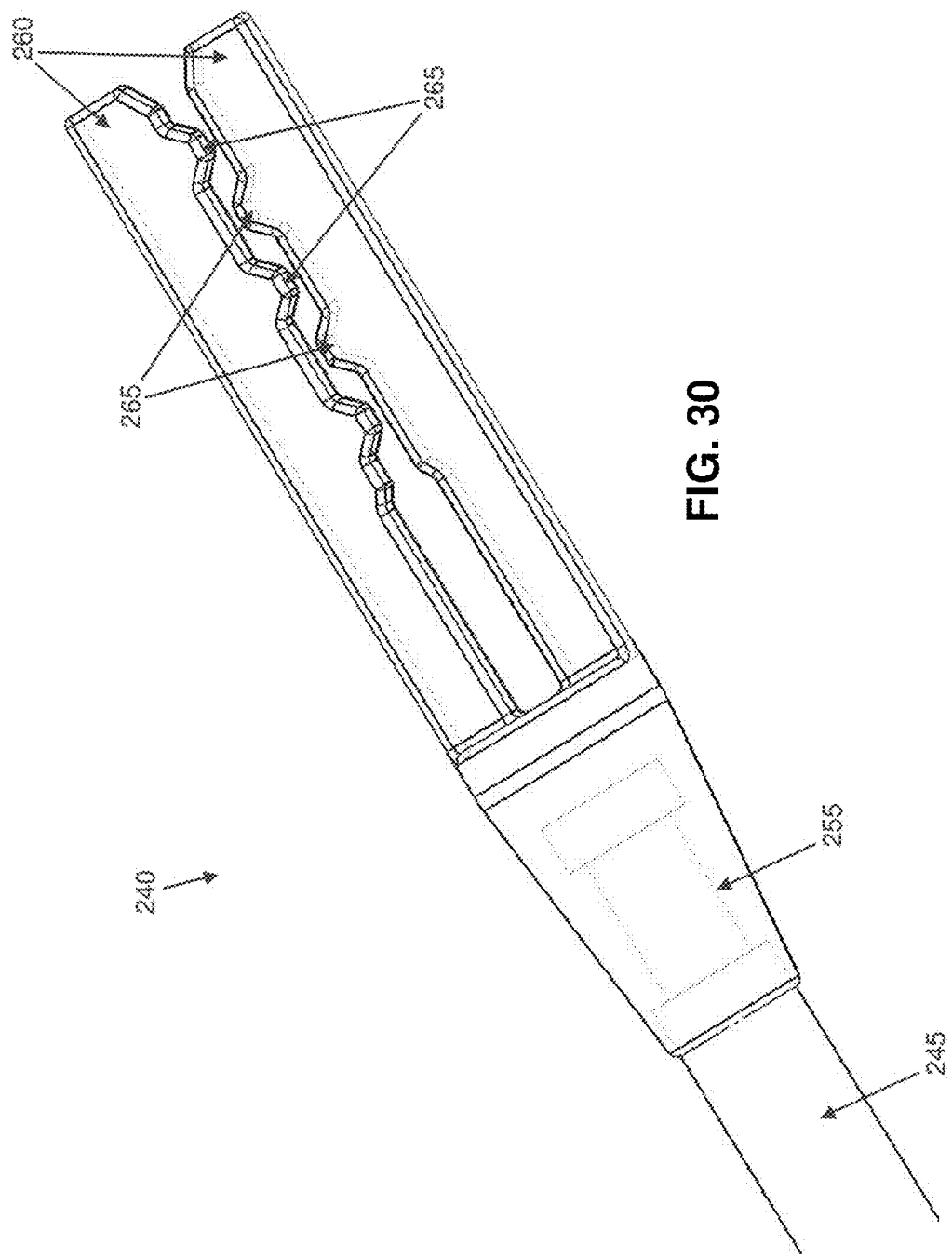
Figure 31:
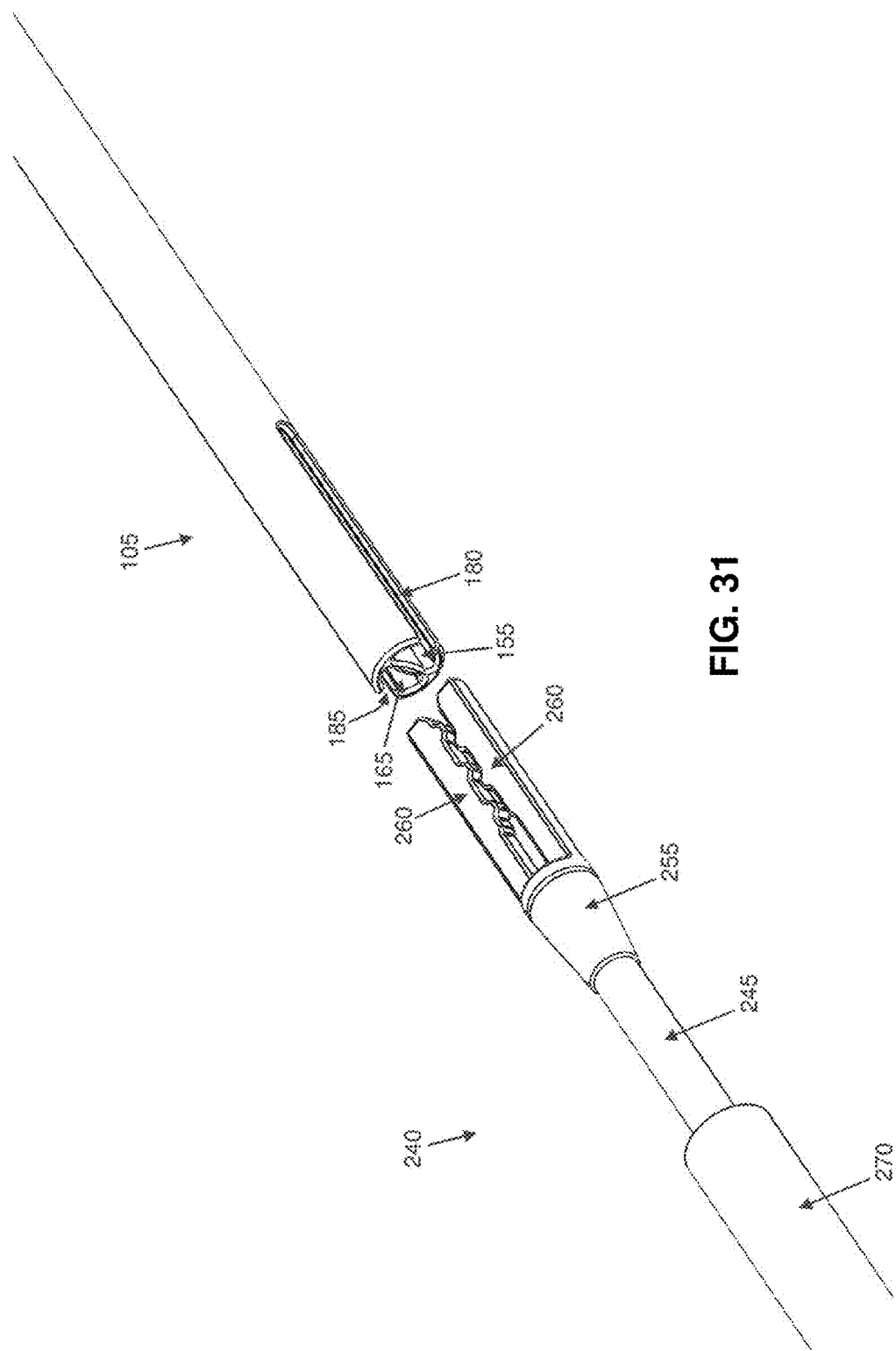
Figure 32:
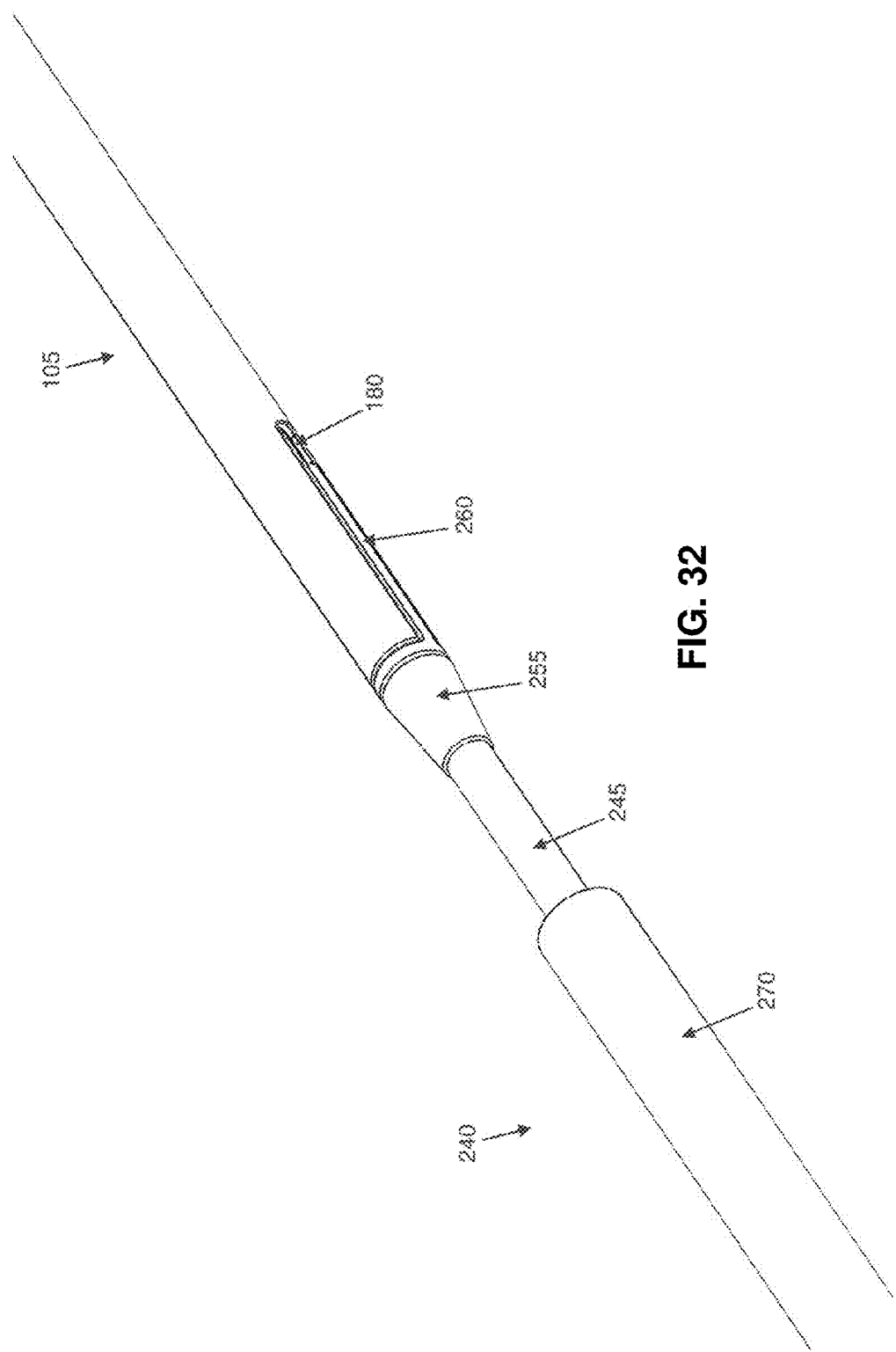
Figure 33:
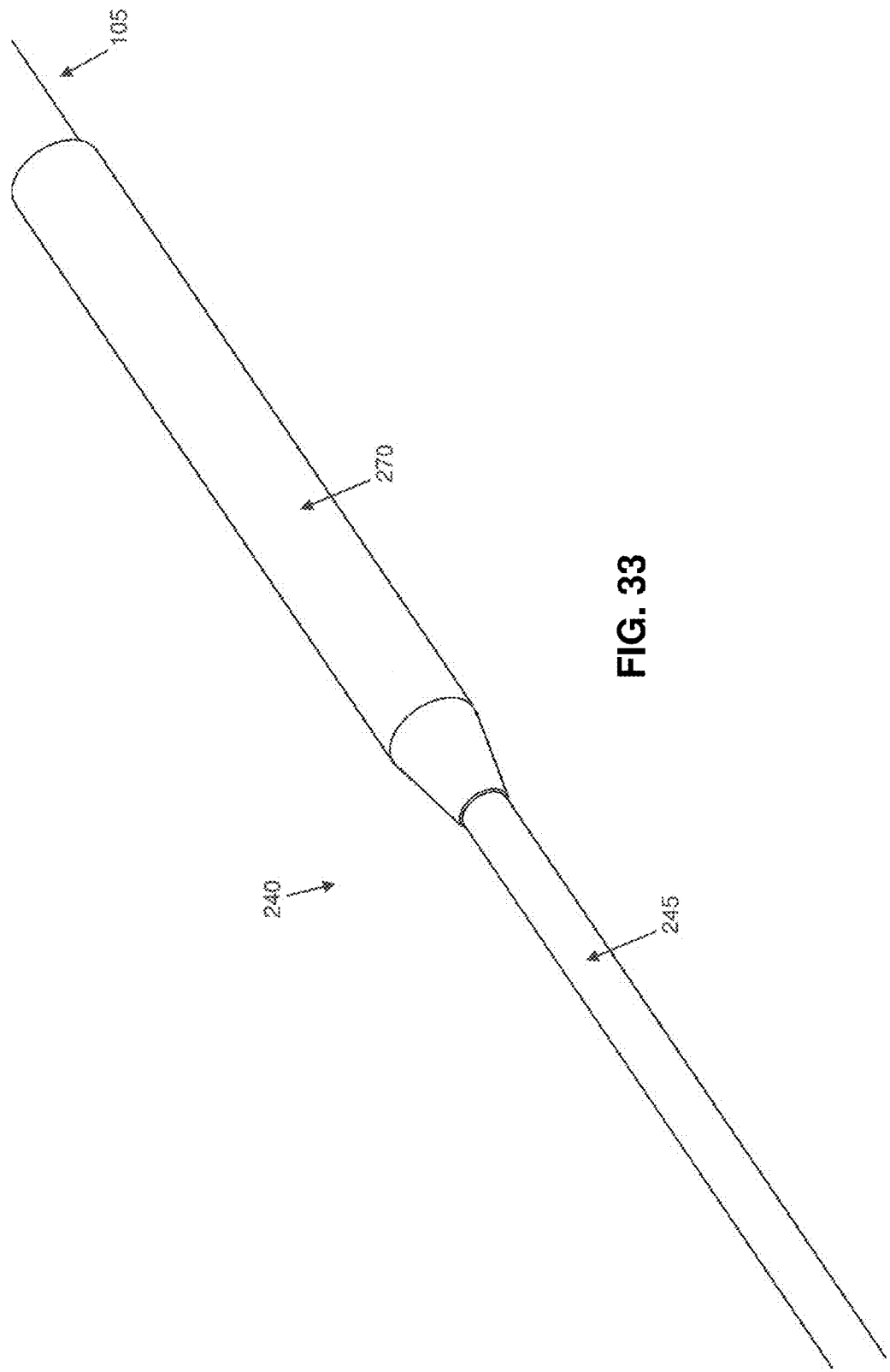
Figure 34:
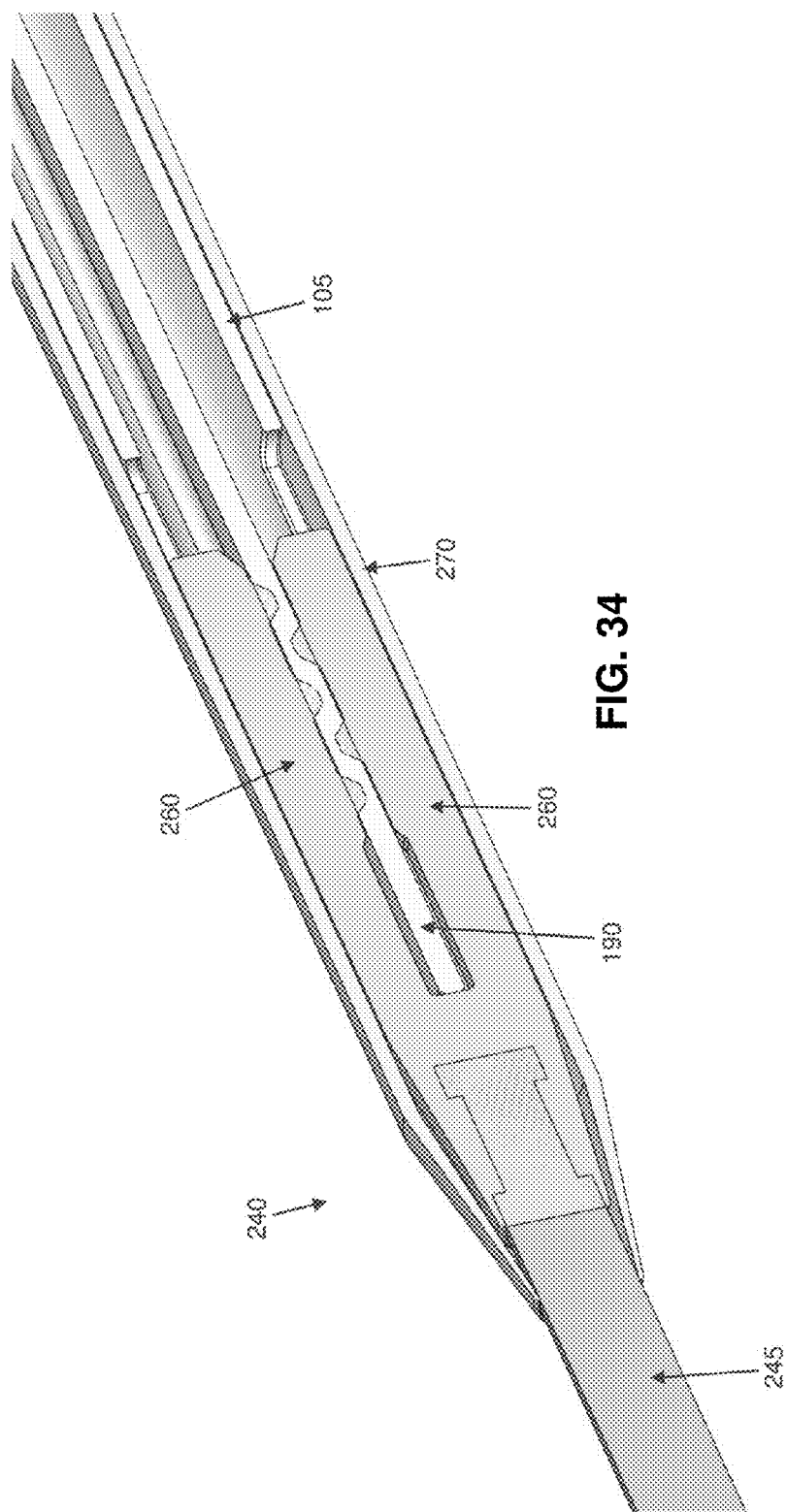

The procedure for deploying a hemodialysis catheter in this manner will now be described, with reference being made to FIG. 26 of the figures:
1. locate the jugular vein 40 which is to be accessed;
2. make a first incision 225 into the skin near the jugular vein;
3. use the Seldinger technique to access the jugular vein, i.e., place a guidewire (not shown) into the jugular vein, and then place an introducer sheath (not shown) over the guidewire and into the jugular vein;
4. make a second incision 230 into the skin on the chest;
5. advance the hemodialysis catheter, distal end first, through the second incision 230 on the chest, pass the hemodialysis catheter under the skin and then out first incision 225 below the clavicle; and
6. insert the distal end of the hemodialysis catheter into the jugular vein by means of the guidewire and the introducer sheath.

As noted above, in the foregoing Step 5, when the hemodialysis catheter is advanced from the second incision 230 on the chest up to the first incision 225, the hemodialysis catheter is passed distal end first, so that the distal end of the hemodialysis catheter is ready to be passed into the jugular vein of the patient.

In accordance with the present invention, and looking now at FIGS. 27-35, a novel tunneling tool 240 is provided to facilitate advancement of the novel hemodialysis catheter 105, distal end first, under the skin of the patient.

More particularly, tunneling tool 240 generally comprises a shaft 245 terminating at its distal end in a blunt end 250 and terminating at its proximal end in a frustoconical section 255. Frustoconical section 235 supports a pair of substantially parallel fingers 260. Fingers 260 are relatively stiff, but are capable of flexing toward and away from one another. Fingers 260 preferably each include a plurality of projections 265, with the projections 265 of one finger 260 extending toward the opposing finger 260. Fingers 260 have a length and a width such that they can be received in the aforementioned longitudinal slots 180, 185 formed in the distal end of the hemodialysis catheter 105, when the flat distal end surface 175 of the hemodialysis catheter 105 abuts frustoconical section 255. A tapered sleeve 270 is slidably mounted on shaft 230. Sleeve 270 may be slid proximally along shaft 245 and over fingers 260 so as to bend fingers 260 inwardly, in a camming action, whereby to cause the fingers 260 to grip septum 190 of hemodialysis catheter 105, and hence grip the distal end of the hemodialysis catheter, e.g., in the manner of a collet. When the hemodialysis catheter 105 is to be released from tunneling tool 240, tapered sleeve 270 is slid distally, away from the hemodialysis catheter, whereby to allow fingers 260 to relax and thereby release the distal end of the hemodialysis catheter.

Figure 35:
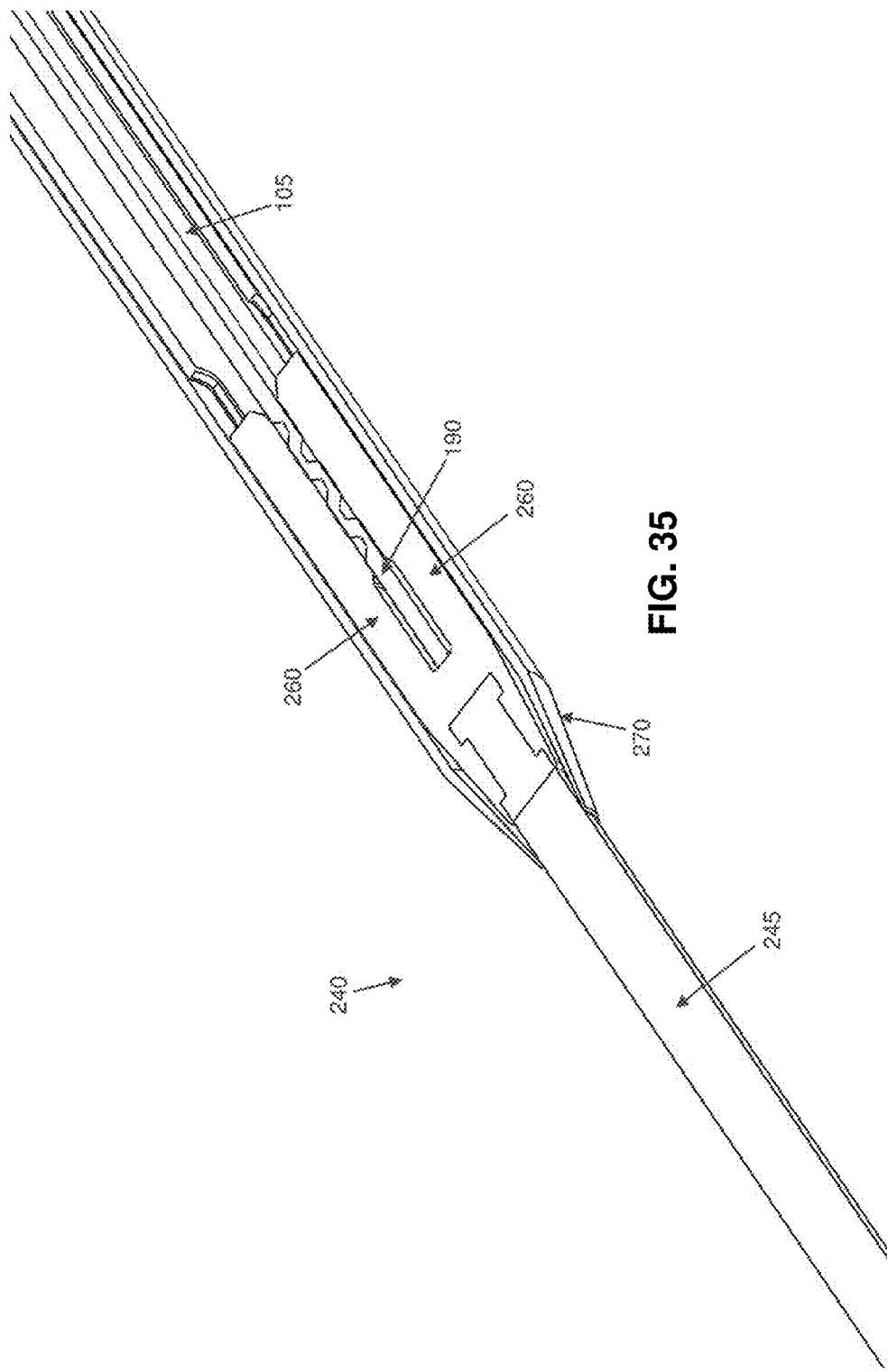
Figure 35A:
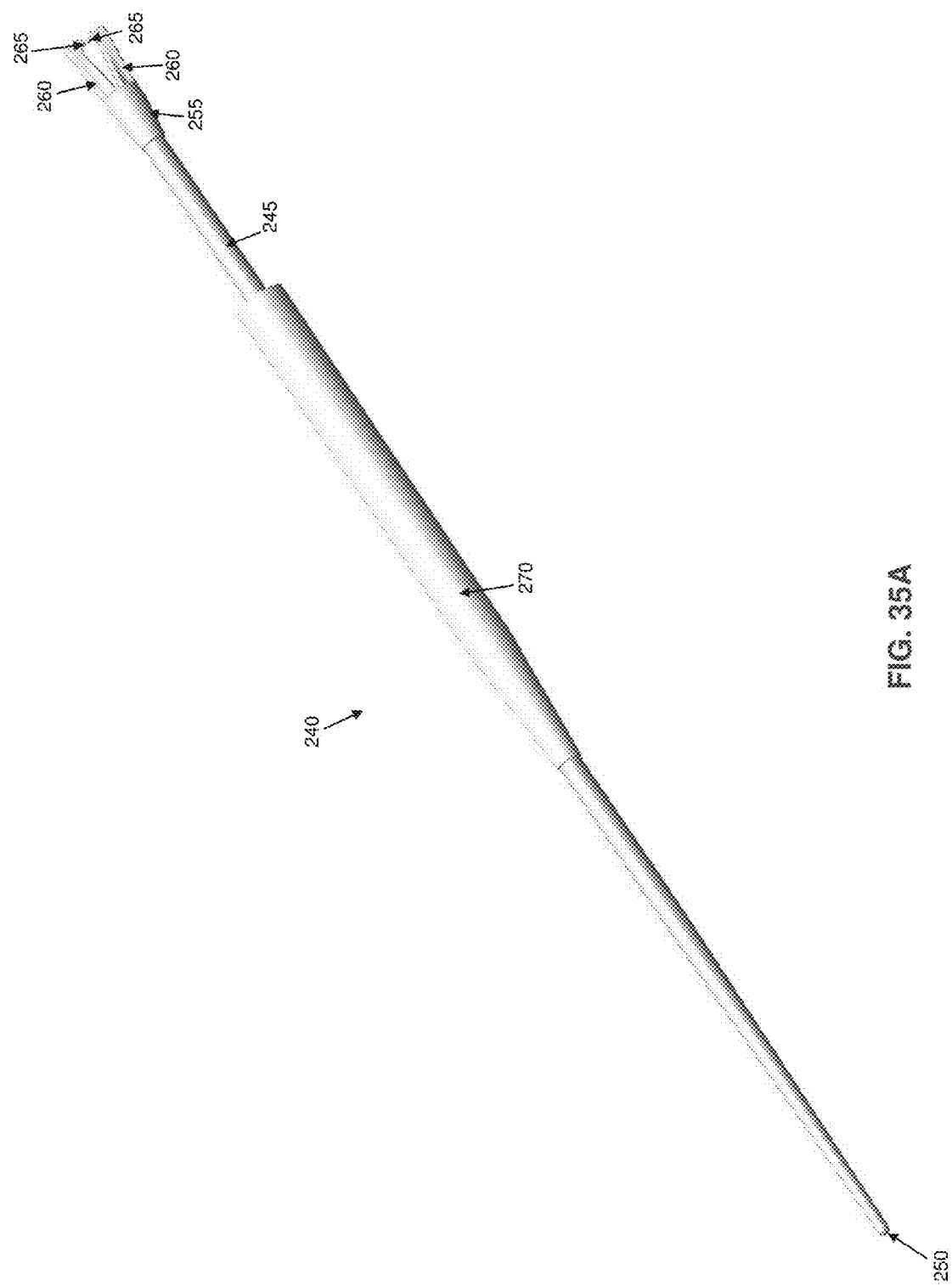
FIGS. 35A and 35B are schematic views showing another form of tunneling tool which may be used in connection with the novel hemodialysis catheter of FIGS. 5 and 6.
Figure 35B:
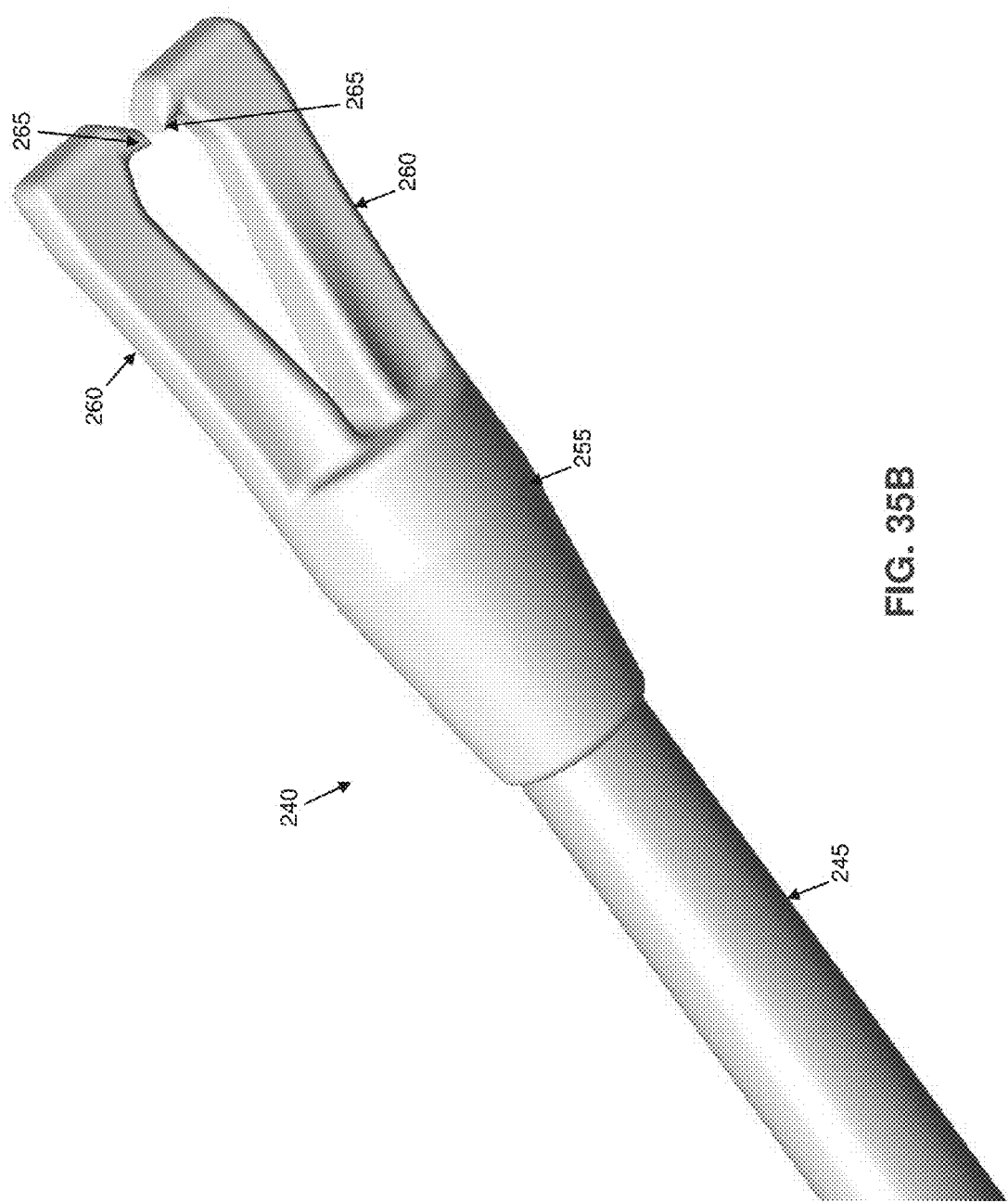

FIGS. 35A and 35B show another form of tunneling tool 240 formed in accordance with the present invention. The construction of tunneling tool 240 shown in FIGS. 35A and 35B is generally similar to the construction of the tunneling tool 240 shown in FIGS. 27-35, except that in FIGS. 35A and 35B, each of the fingers 260 is provided with a single projection 265.

Single Lumen Construction

If desired, and looking now at FIG. 36, two separate single-lumen hemodialysis catheters 275 can be provided in place of hemodialysis catheter 105, where each single-lumen hemodialysis catheter 275 comprises a central lumen 280 terminating in a mouth 285, and has a longitudinal slot 290 extending proximally from mouth 285 and communicating with lumen 280. In this case, single-lumen hemodialysis catheter 275 functions as one half of the complete hemodialysis catheter 105. Again, longitudinal slot 290 is formed with a size (i.e., length and width) adequate to substantially eliminate recirculation even when the mouths 285 of the two single-lumen hemodialysis catheters are disposed substantially adjacent to one another (e.g., within approximately 10 mm of one another).

Apheresis Catheter

Figure 37:
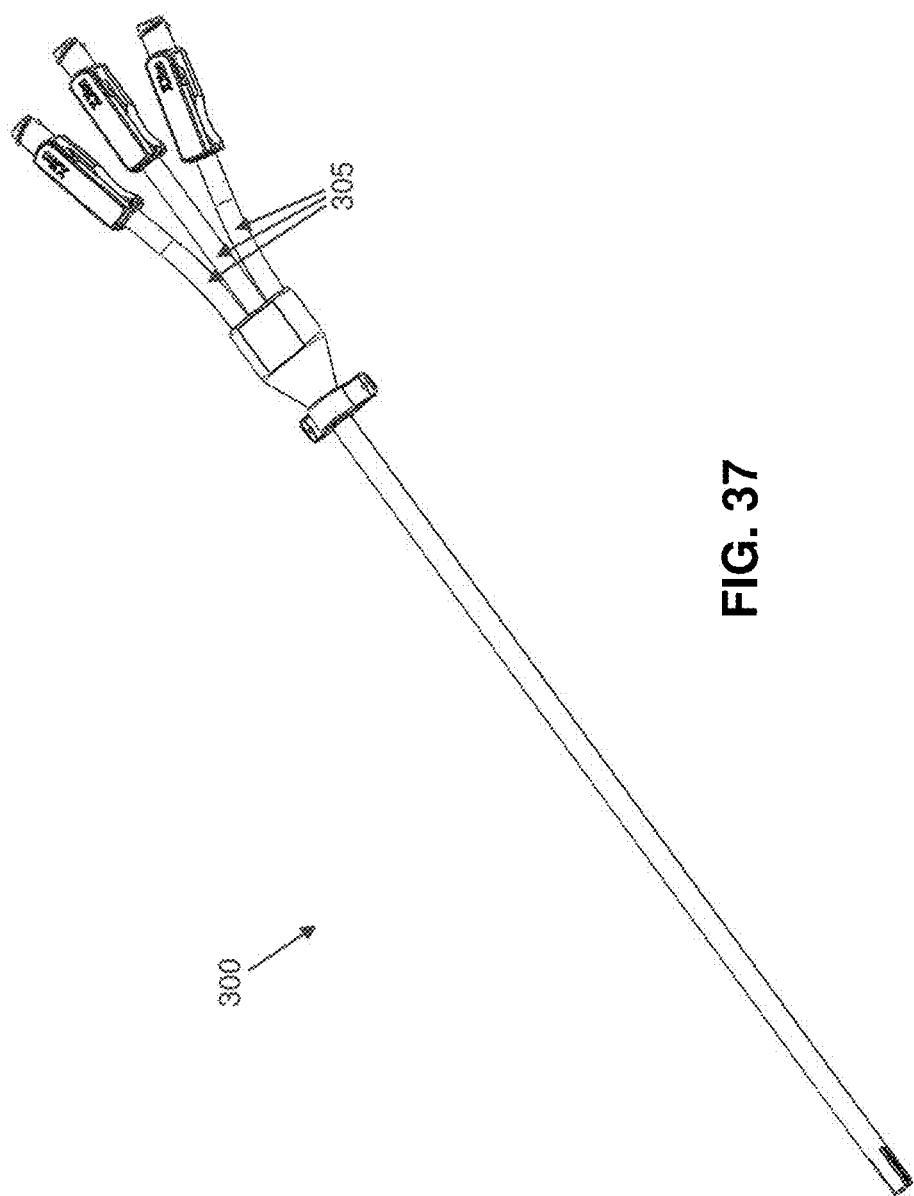
FIGS. 37-39 are schematic views showing a novel apheresis catheter also formed in accordance with the present invention.
Figure 38:
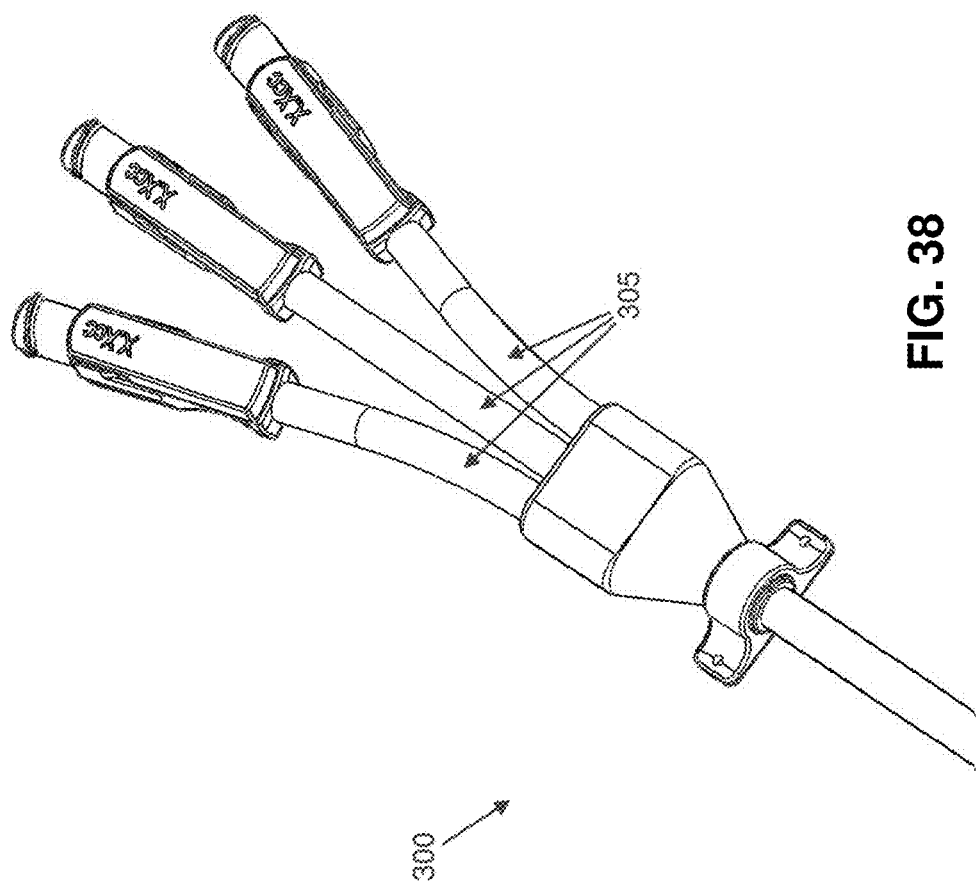
Figure 39:
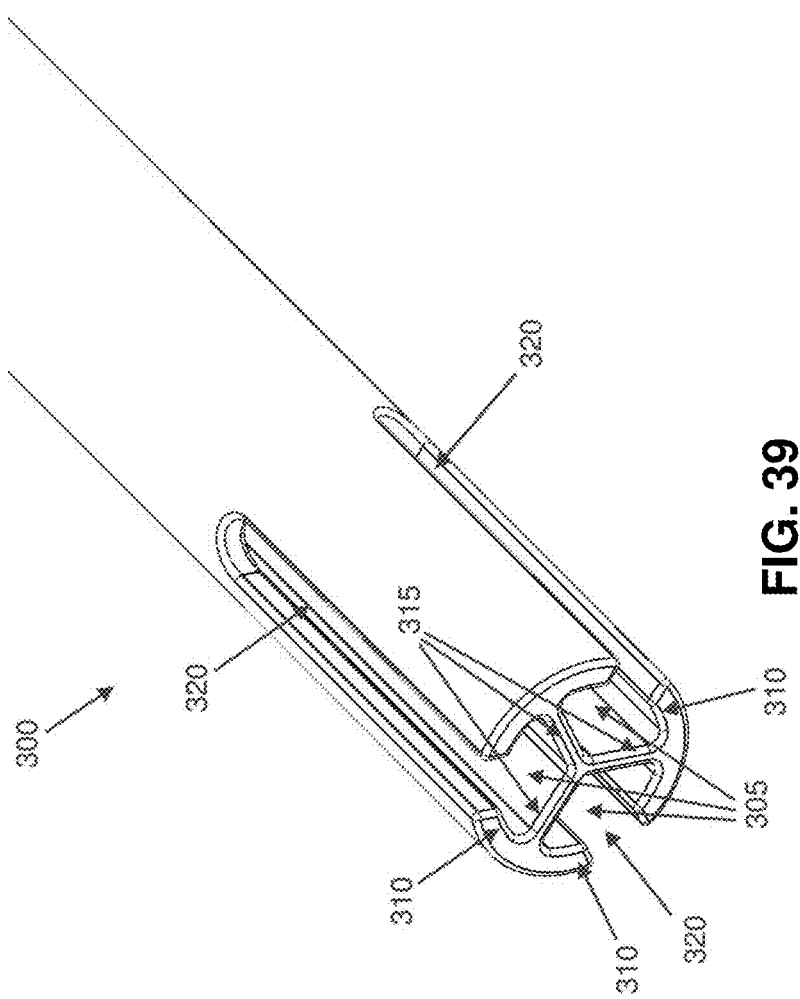

In still another form of the invention, and looking now at FIGS. 37-39, there is provided an apheresis catheter 300 formed in accordance with the present invention. Apheresis catheter 300 is characterized by three or more lumens 305, each terminating in a mouth 310, with septums 315 separating the lumens from one another. Mouths 310 are arranged in a side-by-side configuration. Each of the lumens 305 has a longitudinal slot 320 associated therewith, where each longitudinal slot has a size (i.e., length and width) such that recirculation is substantially eliminated even when one of the lumens is used as a suction line and one of the lumens is used as a return line.

Figure 40:
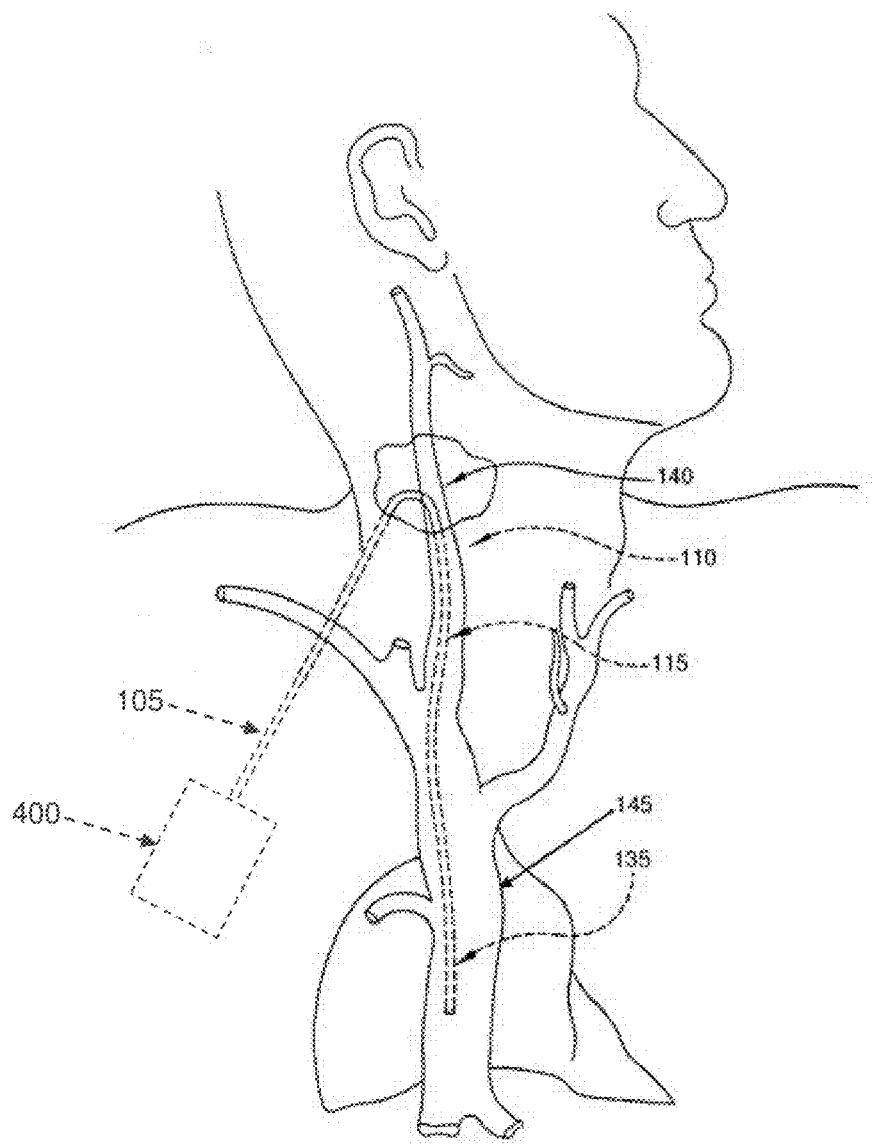
FIG. 40 is a schematic view like that of FIG. 5, except that the two lumen hemodialysis catheter has its connector portion replaced by an implantable port.

Use of the Novel Catheter with an Implantable Port and/or with Other Systems that Exchange Bodily Fluids It should be appreciated that the aforementioned two lumen hemodialysis catheter 105, and/or the aforementioned several single-lumen hemodialysis catheters 275, and/or the aforementioned three or more lumen apheresis catheter 300 may be used in conjunction with an implantable port and/or other systems that exchange (remove and instill) bodily fluids. By way of example but not limitation, FIG. 40 shows one such configuration wherein the two lumen hemodialysis catheter 105 has its connector portion 120 replaced by an implantable port 400.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. Apparatus for use in dialyzing a patient, the apparatus comprising:
   a hemodialysis catheter comprising:
      an elongated body having a proximal end and a distal end, wherein the distal end terminates in a substantially planar distal end surface;
      first and second lumens extending from the proximal end of the elongated body to the distal end of the elongated body,
      wherein the first and second lumens terminate on the substantially planar distal end surface in first and second mouths, respectively, arranged in side-by-side configuration, and
      further wherein the first and second lumens are separated by a septum; and first and second longitudinal slots formed in the distal end of the elongated body and communicating with the interiors of the first and second lumens, respectively, the first and second longitudinal slots opening on the substantially planar distal end surface;

wherein the first and second longitudinal slots each has a length and a width, relative to the dimensions of the first and second lumens and the rate of blood flow to be passed through the hemodialysis catheter, such that (i) when a given lumen is to be used for a return function, the primary blood flow will exit the mouth of that lumen, and (ii) when a given lumen is to be used for a suction function, the primary blood flow will enter the proximal end of the longitudinal slot associated with that lumen, whereby to minimize undesirable recirculation of dialyzed blood.

2. Apparatus according to claim 1 wherein the septum is substantially planar at the distal end of the elongated body, and further wherein the first and second longitudinal slots are set substantially perpendicular to the plane of the septum.

3. Apparatus according to claim 1 wherein the first and second longitudinal slots are sized so that, when the first lumen is used as a suction line and the second lumen is used as a return line, greater than 85% of the flow into the suction line enters the proximal $\frac{1}{3}^{rd}$ of the first longitudinal slot and greater than 85% of the flow out of the return line exits the second mouth of the second lumen.

4. Apparatus according to claim 1 wherein the first and second lumens each have a length of between about 8 mm and 30 mm.

5. Apparatus according to claim 1 wherein the outer surface of the distal end of the elongated body has a substantially circular shape, and further wherein the first and second lumens each have a substantially D-shaped cross-section characterized by a longer dimension and a shorter dimension.

6. Apparatus according to claim 5 wherein the shorter dimension represents the distance between the interior aspect of the first and second longitudinal slots and the corresponding outer surface of the septum.

7. Apparatus according to claim 5 wherein the width of the first and second longitudinal slots is between approximately 30% and 60% of the longer dimension of the D-shaped lumen.

8. Apparatus according to claim 5 wherein the distal end of the hemodialysis catheter has a diameter of 15.5 French, wherein the first and second lumens have a longer dimension of 3.5 mm and a shorter dimension of 1.5 mm, wherein the first and second longitudinal slots have a length of 10 mm and a width of 1.5 mm, and further wherein the rate of blood flow to be passed through the catheter is 350-450 mL per minute.

9. Apparatus according to claim 1 further comprising a first open/close valve disposed across the first lumen, and a second open/close valve disposed across the second lumen, whereby to control flow through the first and second lumens.

10. Apparatus according to claim 9 wherein the first open/close valve comprises a first cylinder extending across the first lumen, the first cylinder having a first through-hole extending therethrough, and the second open/close valve comprises a second cylinder extending across the second lumen, the second cylinder having a second through-hole extending therethrough.

11. Apparatus according to claim 1 further comprising a tunneling tool for drawing the distal end of the hemodialysis catheter through tissue.

12. Apparatus according to claim 11 wherein the tunneling tool comprises a shaft having a distal end and a proximal end, and further wherein the proximal end comprises first and second fingers extending proximally from the shaft.

13. Apparatus according to claim 12 wherein each of the first and second fingers has a length and a width such that the first finger can be accommodated in the first longitudinal slot of the hemodialysis catheter and the second finger can be accommodated in the second longitudinal slot of the hemodialysis catheter.

14. Apparatus according to claim 13 wherein the tunneling tool comprises means for selectively forcing the first and second fingers into locking arrangement with the septum of the hemodialysis catheter.

15. Apparatus according to claim 14 wherein the means for selectively forcing the first and second fingers into locking arrangement with the septum of the hemodialysis catheter comprises a tapered sheath slidably movable along the shaft.

16. Apparatus according to claim 1 wherein the hemodialysis catheter comprises a third lumen extending from the proximal end of the elongated body to the distal end of the elongated body, wherein the third lumen terminates on the substantially planar distal end surface in a third mouth, arranged in side-by-side configuration with the first and second mouths of the first and second lumens, respectively, and further wherein the first, second and third lumens are separated by the septum; and a third longitudinal slot formed in the distal end of the elongated body and communicating with the interior of the third lumen, the third longitudinal slot opening on the substantially planar distal end surface.

17. Apparatus for use in dialyzing a patient, the apparatus comprising:
a hemodialysis catheter system comprising:
a first elongated body having a proximal end and a distal end, wherein the distal end terminates in a first substantially planar distal end surface;
a first lumen extending from the proximal end of the first elongated body to the distal end of the first elongated body, wherein the first lumen terminates on the first substantially planar distal end surface in a first mouth;
a first longitudinal slot formed in the distal end of the first elongated body and communicating with the interior of the first lumen, the first longitudinal slot opening on the first substantially planar distal end surface;
a second elongated body having a proximal end and a distal end, wherein the distal end terminates in a second substantially planar distal end surface;
a second lumen extending from the proximal end of the second elongated body to the distal end of the second elongated body, wherein the second lumen terminates on the second substantially planar distal end surface in a second mouth;
a second longitudinal slot formed in the distal end of the second elongated body and communicating with the interior of the second lumen, the second longitudinal slot opening on the second substantially planar distal end surface;
wherein the first and second longitudinal slots each has a length and a width, relative to the dimensions of the first and second lumens and the rate of blood flow to be passed through the hemodialysis catheter system, such that (i) when a given lumen is to be used for a return function, the primary blood flow will exit the mouth of that lumen, and (ii) when a given lumen is to be used for a suction function, the primary blood flow will enter the proximal end of the longitudinal slot associated with that lumen, whereby to minimize undesirable recirculation of dialyzed blood.

* * * * *